United States Patent
Kaditz et al.

(10) Patent No.: US 10,194,829 B2
(45) Date of Patent: Feb. 5, 2019

(54) FAST SCANNING BASED ON MAGNETIC RESONANCE HISTORY

(71) Applicant: Tesla Health, Inc, Millbrae, CA (US)

(72) Inventors: Jeffrey Howard Kaditz, Wilson, WY (US); Andrew Gettings Stevens, New York, NY (US)

(73) Assignee: Q Bio, Inc., Millbrae, CA (US)

( * ) Notice: Subject to any disclaimer, the term of this patent is extended or adjusted under 35 U.S.C. 154(b) by 19 days.

(21) Appl. No.: 15/169,719

(22) Filed: May 31, 2016

(65) Prior Publication Data

US 2017/0007148 A1    Jan. 12, 2017

Related U.S. Application Data

(60) Provisional application No. 62/281,176, filed on Jan. 20, 2016, provisional application No. 62/255,363, (Continued)

(51) Int. Cl.
*A61B 5/055*    (2006.01)
*A61B 5/00*    (2006.01)

(52) U.S. Cl.
CPC ............ *A61B 5/055* (2013.01); *A61B 5/7207* (2013.01); *A61B 5/7221* (2013.01); *A61B 5/7267* (2013.01); *A61B 5/7282* (2013.01)

(58) Field of Classification Search
CPC ...................................................... A61B 5/055
See application file for complete search history.

(56) References Cited

U.S. PATENT DOCUMENTS

| | | |
|---|---|---|
| 4,729,892 A | 3/1988 | Beall |
| 5,793,210 A | 8/1998 | Pla et al. |

(Continued)

FOREIGN PATENT DOCUMENTS

| | | |
|---|---|---|
| WO | 2014205275 A1 | 12/2014 |
| WO | WO-2015183792 | 12/2015 |
| WO | WO-2016073985 | 5/2016 |

OTHER PUBLICATIONS

"MRI Simulation-Based Evaluation of Image-Processing and Classification Methods" by R. Kwan et al. IEEE Trans Med Imag. vol. 18, No. 11. pp. 1085-1097 Nov. 1999.*

(Continued)

*Primary Examiner* — Tse Chen
*Assistant Examiner* — Jason Ip
(74) *Attorney, Agent, or Firm* — Aurora Consulting LLC; Steven Stupp; Ashley Sloat

(57) ABSTRACT

During operation, a system iteratively captures MR signals of one or more types of nuclei in one or more portions of a biological lifeform based on scanning instructions that correspond to a dynamic scan plan. The MR signals in a given iteration may be associated with voxels having associated sizes at three-dimensional (3D) positions in at least a corresponding portion of the biological lifeform. If the system detects a potential anomaly when analyzing the MR signals from the given iteration, the system dynamically modifies the scan plan based on the detected potential anomaly, a medical history and/or an MR-scan history. Subsequent measurements of MR signals may be associated with the same or different: types of nuclei, portions of the biological lifeform, voxels sizes and/or 3D positions.

23 Claims, 9 Drawing Sheets

Related U.S. Application Data filed on Nov. 13, 2015, provisional application No. 62/253,128, filed on Nov. 9, 2015, provisional application No. 62/250,501, filed on Nov. 3, 2015, provisional application No. 62/245,269, filed on Oct. 22, 2015, provisional application No. 62/233,291, filed on Sep. 25, 2015, provisional application No. 62/233,288, filed on Sep. 25, 2015, provisional application No. 62/213,625, filed on Sep. 3, 2015, provisional application No. 62/189,675, filed on Jul. 7, 2015.

(56) References Cited

U.S. PATENT DOCUMENTS

| | | | |
|---|---|---|---|
| 6,084,408 | A | 7/2000 | Chen |
| 6,148,272 | A | 11/2000 | Bergstrom et al. |
| 6,392,409 | B1 | 5/2002 | Chen |
| 7,924,002 | B2 | 4/2011 | Lu |
| 7,940,927 | B2 | 5/2011 | Futa et al. |
| 7,974,942 | B2 | 7/2011 | Pomroy |
| 8,432,165 | B2 | 4/2013 | Weiger Senften |
| 8,502,532 | B2 | 8/2013 | Assmann |
| 8,686,727 | B2 | 4/2014 | Reddy et al. |
| 8,723,518 | B2 | 5/2014 | Seiberlech et al. |
| 8,736,265 | B2 | 5/2014 | Boernert et al. |
| 9,513,359 | B2 | 12/2016 | Koch |
| 9,514,169 | B2 | 12/2016 | Mattsson |
| 2002/0155587 | A1 | 10/2002 | Opalsky |
| 2002/0177771 | A1 | 11/2002 | Guttman et al. |
| 2003/0210043 | A1 | 11/2003 | Freedman |
| 2005/0137476 | A1* | 6/2005 | Weiland ............. G01R 33/4625 600/416 |
| 2005/0181466 | A1 | 8/2005 | Dambinova |
| 2008/0065665 | A1 | 3/2008 | Pomroy |
| 2008/0081375 | A1 | 4/2008 | Tesiram et al. |
| 2008/0082834 | A1 | 4/2008 | Mattsson |
| 2008/0292194 | A1* | 11/2008 | Schmidt ............... G06T 7/0012 382/217 |
| 2009/0315561 | A1 | 12/2009 | Assmann |
| 2010/0131518 | A1 | 5/2010 | Elteto |
| 2010/0142823 | A1* | 6/2010 | Wang ................ G01R 33/5611 382/195 |
| 2010/0177188 | A1 | 7/2010 | Kishima |
| 2010/0189328 | A1* | 7/2010 | Boernert .......... G01R 33/56375 382/131 |
| 2010/0244827 | A1 | 9/2010 | Hennel |
| 2010/0306854 | A1 | 12/2010 | Neergaard |
| 2011/0095759 | A1 | 4/2011 | Bhattacharya et al. |
| 2011/0166484 | A1 | 7/2011 | Virta |
| 2012/0124161 | A1 | 5/2012 | Tudwell et al. |
| 2013/0275718 | A1 | 10/2013 | Ueda |
| 2013/0294669 | A1 | 11/2013 | El-Baz |
| 2013/0338930 | A1 | 12/2013 | Senegas |
| 2014/0062475 | A1 | 3/2014 | Koch |
| 2014/0336998 | A1 | 11/2014 | Cecchi |
| 2015/0003706 | A1 | 1/2015 | Eftestol et al. |
| 2015/0032421 | A1 | 1/2015 | Dean et al. |
| 2015/0040225 | A1 | 2/2015 | Coates et al. |
| 2015/0089574 | A1 | 3/2015 | Mattsson |
| 2016/0007968 | A1 | 1/2016 | Sinkus |
| 2016/0127123 | A1 | 5/2016 | Johnson |
| 2017/0011514 | A1 | 1/2017 | Westerhoff |
| 2017/0038452 | A1 | 2/2017 | Trzasko |

OTHER PUBLICATIONS

Hasenkam et al. "Prosthetic Heart Valve Evaluation by Magnetic Resonance Imaging." European Journal of Cardio-Thoracic Surgery 1999, pp. 300-305, 16, [Retrieved Aug. 25, 2016] <http://ejcts.oxfordjournals.org/content/16/3/300.full.pdf+html>.

Nestares, et al. "Robust Multiresolution Alignment of MRI Brain Volumes." Magnetic Resonance in Medicine 2000, pp. 705-715, [Retrieved Aug. 27, 2016] <http://web.mit.edu/ImagingPubs/Coregistration/nestares_heeger_coreg.pdf>.

International Search Report and Written Opinion dated Nov. 28, 2016 re PCT/US16/51204.

International Search Report and Written Opinion dated Sep. 19, 2016 re PCT/US16/040578.

International Search Report and Written Opinion dated Sep. 19, 2016 re PCT/US16/040215.

"International Application Serial No. PCT/US2017/022842, Written Opinion dated May 23, 2017, PCT report opinion May 23, 2017", 4 pgs.

"International Application Serial No. PCT/US2017/022842, International Search Report dated May 23, 2017, PCT search report May 23, 2017", 2 pgs.

International Application Serial No. PCT/US2017/035073, International Search Report dated Aug. 11, 2017, 2 pgs.

International Application Serial No. PCT/US2017/035071, International Search Report dated Aug. 22, 2017, 2 pgs.

Siemens. Magnetic Resonance Imaging. (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf].

International Application Serial No. PCT/US2017/035073, Written Opinion dated Aug. 11, 2017, 6 pgs.

International Application Serial No. PCT/US2017/035071, Written Opinion dated Aug. 22, 2017, 7 pgs.

Gualda et al. SPIM-fluid: open source light-sheet based platform for high-throughput imaging. Biomed Opt Express (Nov. 1, 2015} vol. 6, No. 11.

G. Schultz, "Magnetic Resonance Imaging with Nonlinear Gradient Fields: Signal Encoding and Image Reconstruction" Springer Verlag, New York, 2013), Chapter 2.

International Application Serial No. PCT/US2017/022911, International Search Report dated Jul. 19, 2017, 4 pgs.

International Application Serial No. PCT/US2016/040215, International Preliminary Report on Patentability and Written Opinion dated Jan. 9, 2018.

International Application Serial No. PCT/US2017/022911, Written Opinion dated Jul. 19, 2017, 10 pgs.

* cited by examiner

FAST SCANNING BASED ON MAGNETIC RESONANCE HISTORY

CROSS-REFERENCE TO RELATED APPLICATION

The is application claims priority under 35 U.S.C. § 119(e) to: U.S. Provisional Application Ser. No. 62/189,675, entitled "Systems and Method for Indexed Medical Imaging of a Subject Over Time," by Jeffrey H. Kaditz and Andrew G. Stevens, filed on Jul. 7, 2015; U.S. Provisional Application Ser. No. 62/213,625, entitled "Systems and Method for Indexed Medical Imaging of a Subject Over Time," by Jeffrey H. Kaditz and Andrew G. Stevens, filed on Sep. 3, 2015; U.S. Provisional Application Ser. No. 62/233,291, entitled "Systems and Method for Indexed Medical Imaging of a Subject Over Time," by Jeffrey H. Kaditz and Andrew G. Stevens, filed on Sep. 25, 2015; U.S. Provisional Application Ser. No. 62/233,288, entitled "Systems and Method for Indexed Medical and/or Fingerprinting Tissue," by Jeffrey H. Kaditz and Andrew G. Stevens, filed on Sep. 25, 2015; U.S. Provisional Application Ser. No. 62/245,269, entitled "System and Method for Auto Segmentation and Generalized MRF with Minimized Parametric Mapping Error Using A Priori Knowledge," by Jeffrey H. Kaditz, filed on Oct. 22, 2015; U.S. Provisional Application Ser. No. 62/250,501, entitled "System and Method for Auto Segmentation and Generalized MRF with Minimized Parametric Mapping Error Using A Priori Knowledge," by Jeffrey H. Kaditz, filed on Nov. 3, 2015; U.S. Provisional Application Ser. No. 62/253,128, entitled "System and Method for Auto Segmentation and Generalized MRF with Minimized Parametric Mapping Error Using A Priori Knowledge," by Jeffrey H. Kaditz, filed on Nov. 9, 2015; U.S. Provisional Application Ser. No. 62/255,363, entitled "System and Method for Auto Segmentation and Generalized MRF with Minimized Parametric Mapping Error Using A Priori Knowledge," by Jeffrey H. Kaditz, filed on Nov. 13, 2015; and U.S. Provisional Application Ser. No. 62/281,176, entitled "System and Method for Auto Segmentation and Generalized MRF with Minimized Parametric Mapping Error Using A Priori Knowledge," by Jeffrey H. Kaditz, filed on Jan. 20, 2016, the contents of each of which are herein incorporated by reference.

BACKGROUND

Field

The described embodiments relate generally magnetic resonance (MR), more specifically to performing MR scans based on longitudinal MR histories of one or more individuals and/or medical histories of the individuals. More generally, the described embodiments relate to performing non-invasive medical imaging (such as computed tomography, ultrasound or MR imaging) based on longitudinal imaging histories of the one or more individuals and/or the medical histories of the individuals.

Related Art

Magnetic resonance or MR (which is often referred to as 'nuclear magnetic resonance' or NMR) is a physical phenomenon in which nuclei in a magnetic field absorb and re-emit electromagnetic radiation. For example, magnetic nuclear spins may be partially aligned (or polarized) in an applied external magnetic field. These nuclear spins may precess or rotate around the direction of the external magnetic field at an angular frequency (which is sometimes referred to as the 'Larmor frequency') given by the product of a gyromagnetic ratio of a type of nuclei and the magnitude or strength of the external magnetic field. By applying a perturbation to the polarized nuclear spins, such as one or more radio-frequency (RF) pulses (and, more generally, electromagnetic pulses) having pulse widths corresponding to the angular frequency and at a right-angle or perpendicular to the direction of the external magnetic field, the polarization of the nuclear spins can be transiently changed. The resulting dynamic response of the nuclear spins (such as the time-varying total magnetization) can provide a wealth of information about the physical and material properties of a sample.

In medicine, MR has been widely used to non-invasively determine anatomical structure and/or the chemical composition of different types of tissue. For example, in magnetic resonance imaging (MRI), the dependence of the angular frequency of precession of nuclear spins (such as protons or the isotope $^1$H) on the magnitude of the external magnetic field is used to determine images of anatomical structure. In particular, by applying a non-uniform or spatially varying magnetic field to a patient, the resulting variation in the angular frequency of precession of $^1$H spins is typically used to spatially localize the measured dynamic response of the $^1$H spins to voxels, which can be used to generate images of the internal anatomy of the patient.

However, existing approaches to MRI are typically time-consuming. For example, acquiring MR images with high-spatial resolution (i.e., small voxels sizes) often involves a large number of measurements (which are sometimes referred to as 'scans') to be performed. Moreover, in order to achieve high-spatial resolution, a large homogenous external magnetic field is usually used during MRI. The external magnetic field is typically generated using a super-conducting magnet having a toroidal shape with a narrow bore, which can feel confining to many patients.

The combination of long scan times and the confining environment of the magnet bore can degrade the user experience during MRI. Indeed, some patients feel profoundly claustrophobic in MR scanners. In addition, long scan times reduce throughput, thereby increasing the cost of performing MM.

SUMMARY

Some embodiments relate to a system that performs an MR scan. This system includes: an MR scanner that, during operation, performs one or more MR scans of at least a first portion of a biological lifeform; and an interface circuit that, during operation, communicates information with the MR scanner. Moreover, during operation, the system: provides, to the MR scanner, first scanning instructions based on an initial scan plan to capture first MR signals of one or more first types of nuclei in at least the first portion of the biological lifeform, where the first MR signals are associated with first voxels having first sizes at first three-dimensional (3D) positions in at least the first portion of the biological lifeform; receives, from the MR scanner, the first MR signals; and analyzes the first MR signals to detect a potential anomaly in the first MR signals based on: a medical history of the biological lifeform; an MR-scan history of the biological lifeform that includes prior MR scans of the biological lifeform; and/or a first template of a potential anomaly. Furthermore, the system dynamically modifies the initial scan plan based on the detected potential anomaly, the medical history and/or the MR-scan history, where the modified scan plan includes one or more second types of nuclei in second voxels, having associated second sizes, in at least a second portion of the biological lifeform, and where the second sizes are different than the first sizes. Additionally, the system: provides, to the MR scanner, second scanning instructions based on the modified scan plan to capture second MR signals of the one or more second types of nuclei in at least the second portion of the biological lifeform, where the second MR signals are associated with the second voxels at second 3D positions in at least the second portion of the biological lifeform; and receives, from the MR scanner, the second MR signals.

In some embodiments, the system generates the initial scan plan for at least the first portion of the biological lifeform based on the medical history and the MR-scan history, where the initial scan plan may include the one or more first types of nuclei in the first voxels, having the first sizes, in at least the first portion of the biological lifeform.

Note that the first template of the potential anomaly may include simulated MR signals of the one or more first types of nuclei at the first voxels in at least the biological lifeform. In some embodiments, the system generates the simulated MR signals. For example, the generating of the simulated MR signals may involve: resampling predetermined MR signals; interpolating the predetermined simulated MR signals at the first voxels; and/or calculating the simulated MR signals using a previously determined invariant MR signature, predetermined characteristics of the MR scanner and the initial scanning instructions.

Moreover, the system may classify each of the voxels associated with the detected potential anomaly as having: a risk of misclassification that is less than a threshold value; the risk misclassification that is greater than the threshold value; and/or the risk misclassification that is unknown. Note that at least the second portion of the biological lifeform may correspond to the 3D positions of the detected potential anomaly. Furthermore, the second voxels sizes and at least the second portion of the biological lifeform may be computed from a size of the detected potential anomaly. In some embodiments, the system updates, based on additional information (such as additional MR scans on the same or another biological lifeform, etc.) the classification; and changes a recommended time for a subsequent MR scan based on the updated classification.

Additionally, the system may analyze the second MR signals to refine the detected potential anomaly based on one or more of: the medical history; the MR-scan history; and/or a second template of the potential anomaly. Note that the second template of the potential anomaly may include simulated MR signals of the one or more second types of nuclei at the second voxels in at least the biological lifeform.

Note that the first MR signals may include a first MR image and the second MR signals may include a second MR image.

Moreover, the second scanning instructions may correspond to: magnetic-resonance spectroscopy (MRS), magnetic-resonance thermometry (MRT), magnetic-resonance elastography (MRE), MR fingerprinting (MRF), and diffusion-tensor imaging.

Furthermore, the system may analyze adjacent voxels associated with the detected potential anomaly to determine a metabolic chemical signature in MRS. In some embodiments, the analysis of the first MR signals includes instructions for aligning the first MR signals in the first voxels with anatomical landmarks of the biological lifeform in a prior MR scan of the biological lifeform and comparing the aligned first MR signals in the first voxels with prior first MR signals in the first voxels in the prior MR scan. For example, the aligning may involve performing point-set registration.

Note that the second voxel sizes and at least the second portion of the biological lifeform may be based on a location in the biological lifeform of the potential anomaly.

Additionally, the system may: provide, to the MR scanner, third scanning instructions based on the initial scan plan to capture third MR signals of the one or more first types of nuclei in a third portion of the biological lifeform, where the third MR signals are associated with the first voxels at third 3D positions in at least the third portion of the biological lifeform; and receive, from the MR scanner, the third MR signals, where the third MR signals complete the initial scan plan that was interrupted to capture the second MR signals.

Moreover, the system may determine the recommended time for a subsequent MR scan of the biological lifeform based on one or more of: the medical history; the MR-scan history; and the detected potential anomaly.

Furthermore, the system may dynamically modify the initial scan plan based on detection of the potential anomaly or another potential anomaly in a second biological lifeform.

In some embodiments, the system includes a processor and memory that stores a program module. During operation, the processor executes the program module to perform scans of the biological lifeform.

Another embodiment provides a computer-program product for use with an MR scanner. This computer-program product includes instructions for at least some of the aforementioned operations performed by the system.

Another embodiment provides a method for performing an MR scan using an MR scanner. This method includes at least some of the aforementioned operations performed by the system.

This Summary is provided for purposes of illustrating some exemplary embodiments, so as to provide a basic understanding of some aspects of the subject matter described herein. Accordingly, it will be appreciated that the above-described features are simply examples and should not be construed to narrow the scope or spirit of the subject matter described herein in any way. Other features, aspects, and advantages of the subject matter described herein will become apparent from the following Detailed Description, Figures, and Claims.

Figure 1:
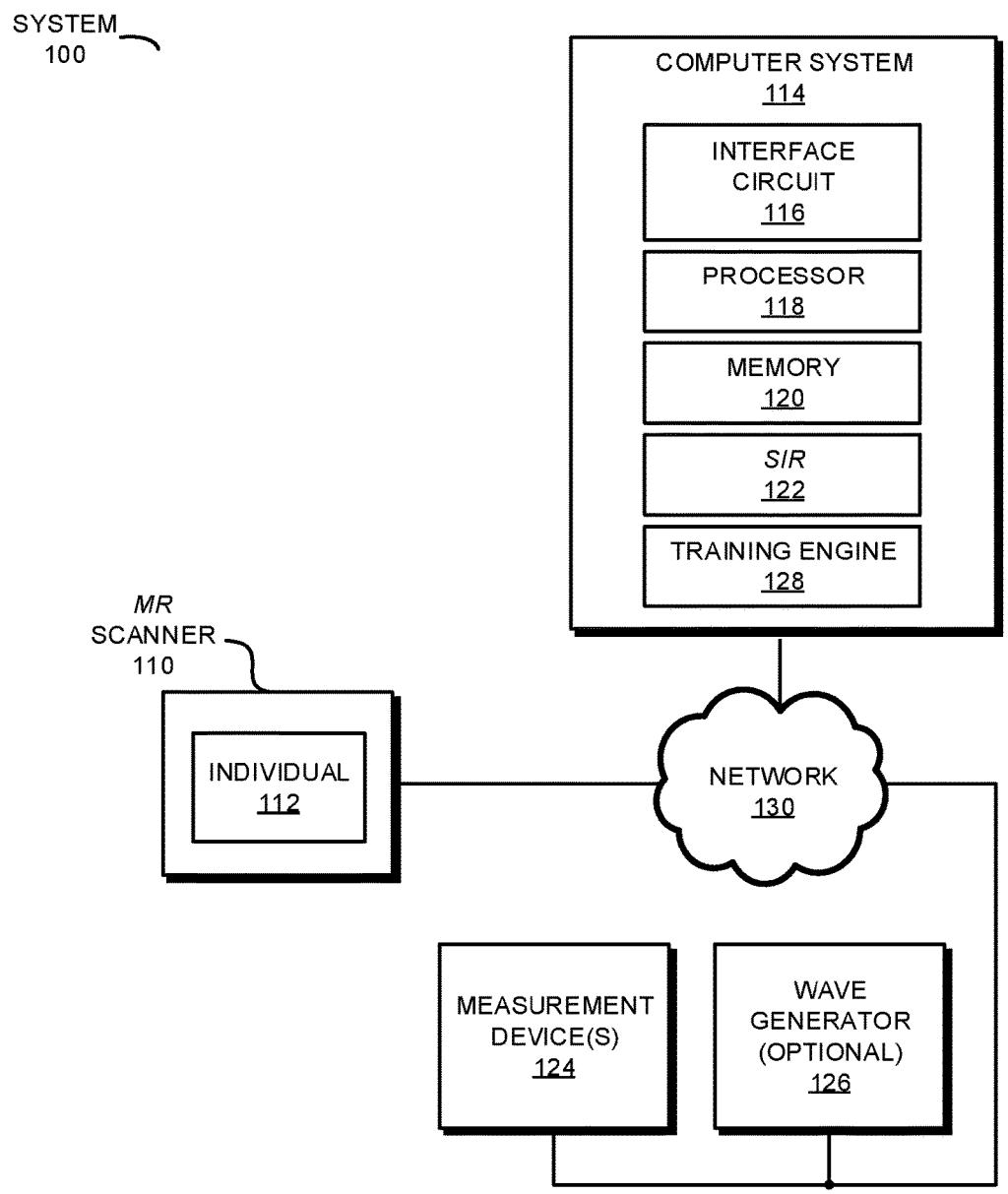
FIG. 1 is a block diagram illustrating a system with a magnetic-resonance (MR) scanner that performs an MR scan of a biological lifeform in accordance with an embodiment of the present disclosure.

Table 1 provides spin-lattice ($T_1$) and spin-spin ($T_2$) relaxation times in different types of tissue in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

During operation, a system iteratively captures MR signals of one or more types of nuclei in one or more portions of a biological lifeform (such as a person) based on scanning instructions that correspond to a dynamic scan plan. The MR signals in a given iteration may be associated with voxels having associated sizes at 3D positions in at least a corresponding portion of the biological lifeform. If the system detects a potential anomaly when analyzing the MR signals from the given iteration, the system dynamically modifies the scan plan based on the detected potential anomaly, a medical history and/or an MR-scan history. Subsequent measurements of MR signals may be associated with the same or different: types of nuclei, portions of the biological lifeform, voxel sizes and/or 3D positions.

By dynamically updating the scan plan (and, thus, the acquired or captured MR signals), this measurement technique may facilitate fast MR scans. For example, an initial MR scan may use an initial voxel size, and a subsequent MR scan may use a finer voxel size in a portion of the biological lifeform that is of interest, such as a specific anatomical region where a potential anomaly was detected. Note that the voxel size(s) may or may not be isometric. Moreover, instead of voxels, imaging can be performed using tomographic slicing.

In addition, the measurement technique may allow the scan plan to be updated based on the medical history of one or more biological lifeforms and/or the scan history of the one or more biological lifeforms, which may include one or more prior MR scans of the one or more biological lifeforms. This approach may allow knowledge obtained for the same and/or different individuals to be used to perform the MR scans in an intelligent manner. For example, the one or more prior MR scans (which were performed on another occasion) and/or the medical history may allow the specific medical circumstances of an individual to be determined and used to guide subsequent MR scans. Over time, therefore, the measurement technique may allow increased focus (e.g., at higher resolution) at one or more predicted regions of interest in an individual. The one or more prior MR scans may also be used as a quantitative baseline during analysis of the subsequent MR scans, which may improve the accuracy of the analysis and may reduce the time and the signal-to-noise ratio (SNR) needed for accurate detection of a potential anomaly.

Consequently, the measurement technique may reduce the time and, thus, may increase the throughput associated with MR scans, such as in MRI and/or another MR technique. The increased throughput may significantly reduce the cost of the MR scans. Moreover, the reduction in the scan time may improve the user experience by reducing the amount of time people spend in the confining environment of a magnet bore in an MR scanner. In addition, the use of a quantitative baseline may facilitate quantitative analysis of the MR scans and may improve the accuracy of the MR scans, which may reduce medical errors, thereby improving the health and well-being of people.

Note that the quantitative analysis of the MR scans in the measurement technique may be facilitated by the use of MR fingerprints of biological lifeforms that are magnetic-field invariant (which are sometimes referred to as 'magnetic-field-invariant MR signatures' or 'invariant MR signatures'). The invariant MR signatures may describe the dynamic MR responses of voxels at 3D positions in the one or more biological lifeforms at arbitrary magnetic-field strengths. Moreover, the invariant MR signatures may be independent of the MR scanners, as well as the specific scanning instructions (e.g., magnetic-field strengths and/or pulse sequences), used to acquire MR signals in a variation on MRF (which is sometimes referred to as 'quantitative MRF' or QMR-X) that were then used to determine the invariant MR signatures. As described further below, an invariant MR signature may be determined by iteratively converging MR signals of one or more types of nuclei in a biological lifeform, which were acquired by an MR scanner based on scanning instructions, with simulated MR signals (which are sometimes referred to as calculated MR signals or estimated MR signals) for the biological lifeform that are generated using an MR model and the scanning instructions.

In the discussion that follows, the measurement technique may be used in conjunction with a variety of MR techniques, including: MRI, MRS, magnetic resonance spectral imaging (MRSI), MRF, MRE, MRT, magnetic-field relaxometry, diffusion-tensor imaging and/or another MR technique (such as functional MRI, metabolic imaging, molecular imaging, blood-flow imaging, etc.). Note that these MR techniques are each a form of quantitative tensor-field mapping.

In particular, 'MRI' should be understood to include generating images (such as 2D slices) or maps of internal structure in a sample (such as anatomical structure in a biological sample, e.g., a tissue sample or a patient) based on the dynamic response of a type of nuclear spin (such protons or the isotope $^1$H) in the presence of a magnetic field, such as a non-uniform or spatially varying external magnetic field (e.g., an external magnetic field with a well-defined spatial gradient). Moreover, MRS should be understood to include determining chemical composition or morphology of a sample (such as a biological sample) based on the dynamic response of multiple types of nuclear spins (other than or in addition to $^1$H) in the presence of a magnetic field, such as a uniform external magnetic field.

Furthermore, MRST should be understood to include generating images or maps of internal structure and/or chemical composition or morphology in a sample using MRS in the presence of a magnetic field, such as a non-uniform or spatially varying external magnetic field. For example, in MRSI the measured dynamic response of other nuclei in addition to $^1$H are often used to generate images of the chemical composition or the morphology of different types of tissue and the internal anatomy of a patient.

Additionally, in contrast with existing approaches to MRI or MRSI that usually provide qualitative or 'weighted' measurements of a limited set of properties, 'MRF' should be understood to include quantitative measurements of the properties of a sample by acquiring signals representing a dynamic or time-dependent magnetization or MR trajectory from different materials in a sample using a pseudorandom pulse sequence. In particular, instead of using repeated, serial acquisition of data to characterize individual parameters that are of interest, in MRF signals from different materials or tissues are often acquired using a pseudorandom pulse sequence to determine a unique signal or 'fingerprint' (e.g., a time-dependent magnetization or MR trajectory). The resulting unique fingerprint of the sample is, in general, a function of multiple material properties under investigation. For example, MRF can provide high-quality quantitative maps of: the spin-lattice relaxation time $T_1$ (which is the time constant associated with the loss of signal intensity as components of the nuclear-spin magnetization vector relax to be parallel with the direction of an external magnetic field), the spin-spin relaxation time $T_2$ (which is the time constant associated with broadening of the signal during relaxation of components of the nuclear-spin magnetization vector perpendicular to the direction of the external magnetic field), proton density (and, more generally, the densities of one or more type of nuclei) and diffusion (such as components in a diffusion tensor).

Note that 'magnetic-field relaxometry' (such as $B_0$ relaxometry with the addition of a magnetic-field sweep) may involve acquiring MR images at different magnetic-field strengths. These measurements may be performed on the fly or dynamically (as opposed to performing measurements at a particular magnetic-field strength and subsequently cycling back to a nominal magnetic-field strength during readout, i.e., a quasi-static magnetic-field strength). For example, the measurements may be performed using untuned radio-frequency (RF) coils or a magnetometer so that measurements at the different magnetic-field strengths can be performed in significantly less time.

Moreover, in the discussion that follows 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

Furthermore, MRT should be understood to include measuring maps of temperature change in a sample using MM.

In the discussion that follows, note that a biological lifeform may include a tissue sample from an animal or a person (i.e., a portion of the animal or the person). For example, the tissue sample may have been previously removed from the animal or the person. In some embodiments, the tissue sample is a pathology sample, such as a biopsy sample. Thus, the tissue sample may be formalin fixed-paraffin embedded. However, in other embodiments a biological lifeform may be in the animal or the person (i.e., an in-vivo sample) and/or the measurement technique involves whole-body scans. Furthermore, the measurement technique may also be applied to inanimate (i.e., non-biological) samples of a wide variety of different materials. In the discussion that follows, the biological lifeform is a person or an individual, which is used as an illustrative example. Moreover, while the measurement technique may be used with a wide variety of non-invasive measurement techniques, in the discussion that follows MR techniques, and in particular MRI and MRS, are used as illustrative examples.

We now describe embodiments of a system. While the pace of technical innovation in computing and MR software and hardware is increasing, today MR scans are still performed and interpreted in an 'analog' paradigm. In particular, MR scans are performed with at best limited context or knowledge about an individual and their pathologies, and typically are based on a limited set of programs that are input by a human operator or technician. Similarly, the resulting MR images are usually read by radiologists based on visual interpretation with at best limited comparisons with prior MR images. The disclosed system and measurement technique leverages a combination of a decreasing cost per clock cycle in the computer industry and a decreasing cost per Tesla of MR hardware to facilitate a digital revolution in MR technology and radiology, with a commensurate impact of accuracy, patient outcomes and overall cost.

The disclosed system and measurement technique leverages the medical histories and prior MR scans of one or more individuals (which collectively are sometimes referred to as 'medical contexts') with one or more MR scanners and additional measurement devices to provide a feedback loop that facilitates targeted, quantitative MR scans at scale. These targeted scans using one or more MR techniques may be performed as needed or periodically, and may be partial scans (such as of regions of interest) or full-body scans. For example, the one or more MR techniques may be used to perform, in series or parallel, soft-tissue measurements, morphological studies, chemical-shift measurements, magnetization-transfer measurements, MRS, measurements of one or more types of nuclei, Overhauser measurements, and/or functional imaging.

Moreover, a given scan may be dynamically modified when a potential anomaly is detected to acquire more detailed diagnostic information. Thus, a region of interest may be scanned using different resolution (i.e., a different voxel size), a different MR technique, a different pulse sequence and, more generally, based on different scanning instructions. In the process, the system may provide more efficient use of resources, such as reducing scan times and/or reducing the effort of radiologists and healthcare providers needed to interpret the scan results. Note that the scans may be acquired for both healthy individuals and individuals with pathologies, i.e., symptomatic and asymptomatic individuals.

Using indexed scans acquired over time and other types data, the system may build multi-dimensional models of the one or more individuals that can be used to monitor the individuals' health and, based on risk factors, may be used to suggest the frequency and types of diagnostic screenings that should be performed on the one or more individuals. Note that the risk factors may be individual-specific and/or may be aggregated risk factors for at least a subset of the one or more individuals. Moreover, the multi-dimensional models may include multi-dimensional data, on a voxel-by-voxel basis, about the volumetric density of particular chemical signatures, atomic nuclei, etc.

Thus, the system may intelligently manage automated or semi-automated analysis of MR scans, as well as the planning and scheduling of the follow-up scans. For example, the system may classify detected potential anomalies (such as 'known healthy' or 'whitelisted tissue,' 'known anomalous' or 'blacklisted tissue' or 'unknown' or 'greylisted tissue') either independently or in conjunction with radiologist feedback. Moreover, the radiologist feedback may be used to adapt future analysis (such as by modifying training datasets for one or more supervised-learning techniques), so that the system is capable of learning and, therefore, can provide improved analysis and recommendations over time on an individual and/or a population basis. The feedback may also allow the system to learn, over time, the differences between different individuals (such as what may be normal for one individual in their medical context, as opposed to for another individual in a different medical context) and to identify new risk factors.

Note that the system may facilitate these capabilities by, as needed, capturing, analyzing, storing and subsequently accessing enormous volumes of data, far more than can be processed by a single radiologist or even a team of radiologists. Consequently, the system and the measurement technique may facilitate a paradigm shift in medical outcomes by 'crawling,' at high spatial and spectral resolution, indexing and searching quantitative MR scans of the one or more individuals.

In some embodiments, the initial scan plan includes an MR scan using a low magnetic field or no magnetic field MR scan (e.g., RF only) or a measurement other than MR, such as synthetic aperture radar (SAR), to scan for ferromagnetic or paramagnetic materials (e.g., metal plates, pins, shrapnel, other metallic or foreign bodies) in an individual's body. Alternatively or additionally, the initial scan may use electron-spin resonance. The initial scan for paramagnetic materials can improve safety in the system when MR scanning is used. This may be useful in case an individual's medical record does not include information about foreign objects, the foreign objects are new or unknown (e.g., shrapnel fragments remaining in a wound or in excised tissue), or in the event of an error. In particular, this 'safety scan' can prevent damage or injury to the individual, and can protect the system from damage. In addition, the size of any ferromagnetic or paramagnetic material can be estimated during the initial scan, and a safe magnetic-field strength for use during the MR scan can be estimated. Conversely, if the individual does not contain any ferromagnetic of paramagnetic materials, one or more higher magnetic-field strengths can be used during one or more subsequent MR scans.

Moreover, in some embodiments the measurement technique uses so-called 'breadth-first indexing' as a form of compressed sensing. In particular, the system may spend more time scanning and modeling interesting or dynamic parts of an individual, and may avoid spending time on parts that are not changing rapidly. Note that 'interesting' regions may be determined based on information gathered in real-time and/or based on historical information about the individual being scanned or other individuals. The breadth-first indexing may employ inference or inductive techniques, such as oversampling and/or changing the voxel size in different regions in the body based on an estimated abundance of various chemical species or types of nuclei (which may be determined using chemical shifts or MRS). As noted previously and described further below, the scan plan in such breath-first indexing may be dynamically updated or modified if a potential anomaly is detected.

In the discussion that follows, a scan plan can include a scan of some or all of an individual's body, as well as a reason or a goal of the scan. For example, a scan plan may indicate different organs, bones, joints, blood vessels, tendons, tissues, tumors, or other areas of interest in an individual's body. The scan plan may specify, directly or indirectly, scanning instructions for an MR scanner that performs the scan. In some embodiments, the scan plan includes or specifies one or more MR techniques and/or one or more pulse sequences. Alternatively, the one or more MR techniques and/or the one or more pulse sequences may be included or specified in the scanning instructions. As described further below, the scanning instructions may include registration of an individual, so that quantitative comparisons can be made with previous MR scans on the same or another occasion. Thus, at runtime, the areas of interest in the scan may be mapped to 3D spatial coordinates based on a registration scan.

The scan plan, as well as the related scanning instructions (such as the voxel size, one or more spectra, one or more types of nuclei, pulse sequences, etc.), may be determined based on a wide variety of information and data, including: instructions from a physician, medical lab test results (e.g., a blood test, urine-sample testing, biopsies, etc.), an individual's medical history, the individual's family history, comparisons against previous MR scan records, analysis of MR signals acquired in a current scan, and/or other inputs. In some embodiments, the MR scan plan is determined based on risk inputs, such as inputs used to determine the individual's risk to pathologies that are included in a pathology knowledge base. The risk inputs can include: age, gender, current height, historical heights, current weight, historical weights, current blood pressure, historical blood pressures, medical history, family medical history, genetic or genomic information for the individual (such as sequencing, next-generation sequencing, RNA sequencing, epigenetic information, etc.), genetic or genomic information of the individual's family, current symptoms, previously acquired MR signals or images, quantitative tensor field maps, medical images, previous blood or lab tests, previous microbiome analysis, previous urine analysis, previous stool analysis, the individual's temperature, thermal-imaging readings, optical images (e.g., of the individual's eyes, ears, throat, nose, etc.), body impedance, a hydration level of the individual, a diet of the individual, previous surgeries, previous hospital stays, and/or additional information (such as biopsies, treatments, medications currently being taken, allergies, etc.).

Based on scanning instructions that are determined from an initial scan plan (such as using predefined or predetermined pulse sequences for particular at-risk pathologies), the system may measure and store for future use MR signals, such as MR signals associated with a 3D slice through the individual. In general, the MR measurements or scans may acquire 2D or 3D information. In some embodiments, the MR measurements include animations of the individual's body or a portion of their body over time, e.g., over weeks, months, years, or shorter timescales, such as during a surgical procedure.

As noted previously, during the measurements the system may perform a registration scan, which may include a fast morphological scan to register, segment, and model a body in 3D space, and to help calibrate noise-cancelation techniques, such as those based on motion of the individual. For example, the system may include optical and thermal sensors, as well as pulse monitoring, to measure motion of the individual associated with their heartbeat and respiration. Note that a scan can be interrupted to re-run a registration scan to make sure an individual has not shifted or moved. Alternatively or additionally, the measured MR signals during a scan may be used to track and correct the motion of the individual. This correction may be performed during a scan (e.g., by aggregating MR signals associated with a voxel at a particular 3D position) and/or subsequently when the MR signals are analyzed.

In some embodiments (such as during MRI), the system may determine segments of the individual's body. This segmentation may be based, at least in part, on a comparison with segments determined in one or more previous scans. Alternatively or additionally, the measurements may include a segmentation scan that provides sufficient information for a segmentation technique to correctly segment at least a portion of the body of the individual being imaged.

Then, the system may analyze the MR signals. This analysis may involve alignment of voxels based on registration of the 3D positions of the voxels in the individual in the current scan with those in one or more previous scan(s) for the same and/or other individuals. Alternatively or additionally, the system may resample and/or interpolate measured or simulated MR signals from the 3D positions of the voxels in the previous scan(s) to the 3D positions of the voxels in the current scan.

During the analysis, the system may compare current and the previous MR signals. Note that the comparison may be facilitated using a look-up table. For example, the system may MR signals from a voxel with a value in a look-up table that is based on simulated MR signals associated with a previous scan. In this way, the system can compare metabolic chemical signatures between adjacent voxels in an MRS scan to detect a potential anomaly or can perform comparisons to MR signals that are a composite of two or more individual's bodies. Thus, the comparison may be performed on a voxel-by-voxel basis.

In some embodiments, the system performs the analysis by computing an invariant MR signature based on MR signals measured in a current scan and/or computes simulated MR signals based on one or more previously determined invariant MR signatures.

Based on the comparison, the system may classify a voxel as: low risk, high risk or unknown risk. For example, a voxel may be classified as indicative of: early-stage cancer, late-stage cancer, or an unknown-stage cancer. In particular, the system may perform automatic quantitative processing of MR signals from the individual voxels based on a library of baseline tissue characterizations or templates. In this way, quantitative MR measurements (such as MRF) based on a scan plan can be used to quantify the health of: particular organs (such as scanning the liver of the individual for cancer), performing assays of blood, detecting known-good and known-bad quantitative signatures of specific tissues (e.g., skin, heart, liver, muscle, bone, etc.), performing post-biopsy analysis, another type of evaluation, etc.

The resulting classifications (including unknown classifications) may be provided to a radiologist (such as via a graphical user interface that is displayed on a display). In particular, the radiologist may provide a classification, identification feedback or verification feedback. The information from the radiologist may be used to update the analysis (such as one or more supervised-learning models, the look-up table and/or the associated classifications).

When a potential anomaly is detected, the system may dynamically revise or modify the scan plan (and, thus, the scanning instructions) based on the detected potential anomaly, as well as possibly one or more of the factors mentioned previously that were used to determine the initial scan plan. For example, the system may change the voxel size, a type of nuclei, the MR technique (such as switching from MRI to MRS), etc. based on the detected potential anomaly. The modified scan plan may include a region that includes or that is around the detected potential anomaly. Thus, the size of the region may be determined based on a size of the detected potential anomaly. Alternatively or additionally, the region in the modified scan plan may be determined based on a location or segment in the individual's body where the potential anomaly is located.

Next, the system may perform additional MR measurements, which are then analyzed and stored for future use. Note that this additional scan may occur after completion of the first or initial scan of the individual. For example, the modified scanning instructions may be queued for execution after the first scan is completed. Alternatively, when the potential anomaly is detected, the first scan may be stopped (i.e., when it is only partially completed) and the partial MR signals may be stored and/or provided to the system. In some embodiments, the system stops the first scan by providing an interrupt to the MR scanner. Then, after the second or the additional scan is completed, the MR scanner may complete the first scan, and the remainder of the MR signals may be stored and/or provided to the system. In order to complete the interrupted or stopped first scan, the MR scanner may save or store information that specifies the current position when it stopped, as well as the scanning context (such as the MR measurement being performed). This positioning and scanning context information may be used by the MR scanner when the first scan is resumed.

After completing the first and/or the second MR scan (or any additional related scans), as well as the associated analysis, the system may determine a recommended time for a follow up scan of the individual based on any detected anomalies (and, more generally, the results of the current MR scan(s) and/or one or more previous MR scans) and/or any of the aforementioned factors that were used to determine the scan plan(s). Moreover, the system may determine a future scan plan for the individual or another individual based on the results of the current MR scan(s) and/or comparisons of the current MR scan(s) with one or more previous MR scans. This capability may allow the system to facilitate monitoring of one or more individuals over time or longitudinally. Furthermore, this approach may allow the feedback from even a single radiologist to impact the future scan plans of one or more individuals.

As described further below, when determining a scan plan and/or analyzing measured or acquired MR signals the system may access a large data structure or knowledge base of invariant MR signatures from multiple individuals (which is sometimes referred to as a 'biovault'), which may facilitate quantitative comparisons and analysis of MR scans. The biovault may include: invariant MR signatures, additional information and/or identifiers of individuals in the data structure (such as unique identifiers for the individuals). Furthermore, the additional information may include diagnostic information or metadata associated with previous measurements on the individuals or tissue samples associated with the individuals, including: weight, size/dimensions, one or more optical images, one or more infrared images, impedance/hydration measurements, data associated with one or more additional MR techniques, demographic information, family histories and/or medical histories. Note that the biovault may include information for symptomatic and/or asymptomatic individuals. (Therefore, the individuals may not solely be healthy or unhealthy. For example, a particular invariant MR signature may be healthy in certain medical contexts, such as for a particular person, but may be unhealthy in another medical context.) Thus, the biovault can be used to characterize healthy tissue, as well as disease or pathology.

FIG. 1 presents a block diagram illustrating an example of a system 100. This system includes: an MR scanner 110 and computer system 114. As described further below with reference to FIG. 8, computer system 114 may include: a networking subsystem (such as an interface circuit 116), a processing subsystem (such as a processor 118), and a storage subsystem (such as memory 120). During operation of system 100, a technician or an MR operator can scan or read in information about an individual 112 using sample-information reader (SIR) 122 to extract information (such as an identifier, which may be a unique identifier) from a label associated with individual 112 (who is used as an illustrative example of a biological lifeform in the discussion that follows). For example, sample-information reader 122 may acquire an image of the label, and the information may be extracted using an optical character recognition technique. More generally, note that sample-information reader 122 may include: a laser imaging system, an optical imaging system (such as a CCD or CMOS imaging sensor, or an optical camera), an infrared imaging system, a barcode scanner, an RFID reader, a QR code reader, a near-field communication system, and/or a wireless communication system.

Alternatively, the technician or the MR operator may input information about individual 112 via a user interface associated with computer system 114. Note that the extracted and/or input information may include: the unique identifier of individual 112 (such as a subject or patient identifier), an age, a gender, an organ or a tissue type being studied, a date of the MR scan, a doctor or practitioner treating or associated with individual 112, the time and place of the MR scan, a diagnosis (if available), etc.

Then, the technician or the MR operator can place individual 112 in MR scanner 110, and can initiate the MR scans (which may involve MRF, MRT, MRE, MRS, magnetic-field relaxometry, etc.) and/or other measurements, e.g., by pushing a physical button or activating a virtual icon in a user interface associated with computer system 114. Note that the same individuals (and, more generally, the same tissue sample or material) can have different MR signals (such as different signal intensities and/or frequencies) in different datasets that are measured in the same MR scanner or in different MR scanners. In general, such measurement-to-measurement variation depends on many factors, including: the particular instance of MR scanner 110, a type or model of MR scanner 110, a set-up of MR scanner 110, the scanning instructions (such as the magnetic-field strengths, magnetic gradients, voxel sizes, the pulse sequences that are applied to individual 112, the MR techniques, the regions of interest in individual 112, one or more voxel sizes and/or the types of nuclei or molecules), a detector in MR scanner 110, and/or one or more signal-processing techniques. For example, the one or more signal-processing techniques may include: gradient-echo imaging, multi-slice imaging, volume imaging, oblique imaging, spin-echo imaging, inversion recovery imaging, chemical contrast agent imaging, fat suppression imaging using spin-echo imaging with saturation pulses before taking regular images, etc.

These challenges are addressed in system 100 in the measurement technique by performing MR scans and comparing the associated MR signals with simulated MR signals based on one or more previously determined invariant MR signatures of at least individual 112, which are independent of (or has significantly reduced sensitivity to) variations in the magnetic-field strength (and, thus, magnetic-field inhomogeneity). Alternatively, the MR signals acquired in the MR scans may be used to determine an invariant MR signature, which may be compared to one or more previously determined invariant MR signatures.

The one or more invariant MR signatures may include the information found in or corresponding to the information in an MR fingerprint at least of individual 112 (such as high-quality quantitative maps of $T_1$, $T_2$, nuclei density, diffusion, velocity/flow, temperature, off-resonance frequency, and magnetic susceptibility). Moreover, the one or more invariant MR signatures may be corrected for measurement-to-measurement variation (including variation that occurs from one MR scanner to another). Alternatively, the one or more invariant MR signatures may include information that corrects for measurement-to-measurement variation and/or that allows a version of an MR image, an MR spectra, an MR fingerprint, etc. to be generated for particular measurement conditions, such as: a particular MR scanner, a particular model of the MR scanner, scanning instructions, a particular detector, etc. Thus, in conjunction with characteristics of a particular MR scanner (such as the model of this particular MR scanner, the scanning instructions, the detector, noise characteristics of the particular MR scanner, magnetic-field inhomogeneity in the particular MR scanner), the one or more invariant MR signatures may be used to generate or calculate a version of an MR image, an MR spectra, an MR fingerprint, etc. as if it were measured by the particular MR scanner. Note that the noise characteristics of the particular MR scanner may depend on the pulse sequence used.

In some embodiments, an invariant MR signature includes parameters in an MR model of voxels in at least individual 112. Because each voxel in the MR model may include multi-dimensional data on the volumetric density of certain chemical signatures and atomic nuclei, the invariant MR signature of individual 112 may be based on an awareness of one or more regions of individual 112. For example, the voxel size in the MR model may depend on an anatomical location in individual 112.

Moreover, system 100 may use the information in the biovault, the MR signals acquired in an initial scan of individual 112 and/or one or more detected potential anomalies to further optimize the scan plan and, thus, scanning instructions (and, more generally, the conditions during the MR measurements) when collecting additional MR signals from individual 112. For example, the extracted and/or input information about individual 112, as well as additional stored information in memory 120 that is accessed based on the unique identifier (such as a medical record or medical history that is linked or queried based on the unique identifier), may be used by computer system 114 to update the scanning instructions (such as different pulse sequences and/or different magnetic-field strengths, e.g., a range of magnetic-field strengths, including 0 T, 6.5 mT, 1.5 T, 3 T, 4.7 T, 9.4 T, and/or 15 T, the MR techniques, the regions of interest in individual 112, the voxel sizes and/or the types of nuclei), the other measurements to perform and, more generally, a scan or analysis plan. In general, the scanning instructions may specify more than a single value of the magnetic-field strength. For example, the scanning instructions may provide or specify a function that describes how the magnetic field will change over time and in space, or multiple functions that specify a 'surface' that can be used to determine the invariant MR signature of individual 112. As described further below with reference to FIG. 2, in some embodiments the magnetic field is physically and/or virtually manipulated to achieve the specified surface. In particular, the magnetic field may be rotated as a function of time, or in embodiments with physically separate ring magnets that generate the magnetic field, the magnetic field may be changed by: changing the physical distance between the ring magnets, changing the orientation of one ring magnet with respect to the other ring magnet, moving a ring magnet along the z axis, etc.

Moreover, as described further below, note that the other measurements may include: impedance measurements, optical imaging, scanning of dimensions of individual 112, weighing individual 112 and/or other tests that may be included in the measurement technique. For example, a gel-covered table in MR scanner 110 can be used to measure an impedance of individual 112 and/or a weight of individual 112. In some embodiments the other measurements probe individual 112 non-destructively (e.g., using electromagnetic or mechanical waves). However, in other embodiments the measurement technique includes integrated therapeutics, such as: proton beam therapy, radiation therapy, magnetically guided nano particles, etc.

In addition, predetermined characterization of MR scanner 110 may be used to determine the scanning instructions. Alternatively, if MR scanner 110 has not already been characterized, system 100 may characterize and store characteristics of MR scanner 110 prior to calculating simulated MR signals or determining the invariant MR signature, so that the characteristic of MR scanner 110 can be used during the measurement technique, such as to determine the scanning instructions. For example, during operation, computer system 114 may characterize MR scanner 110 based on scans of a phantom.

Note that the predetermined characterization of MR scanner 110 may include a mapping or determination of the inhomogeneity of the magnetic field of MR scanner 110 (because the inhomogeneity may depend on the magnetic-field strength, measurements may be performed at different magnetic-field strengths). The predetermined characterization may also include environmental, geographical and/or other parameters. For example, RF pulses generated by a pulse generator in system 100 may vary from one MR scanner to another, and may vary as a function of time because the performance of components may depend on parameters such as: the load, the temperature, the MR coil configuration, amplifiers, humidity, magnetic storms and/or geolocation. Consequently, in addition to MR signals, the RF pulses (and/or the inhomogeneity in the RF pulses) may be measured, e.g., using a signal splitter between an RF pulse generator and an RF (transmission) coil in MR scanner 110. In some embodiments, the magnetic field produced by the RF coil is measured using a test coil. Note that, because a specific pulse sequence may correspond to a specific voxel size, different pulse sequences corresponding to different voxel sizes may be used when characterizing MR scanner 110 and/or when determining the scanning instructions.

Figure 3:
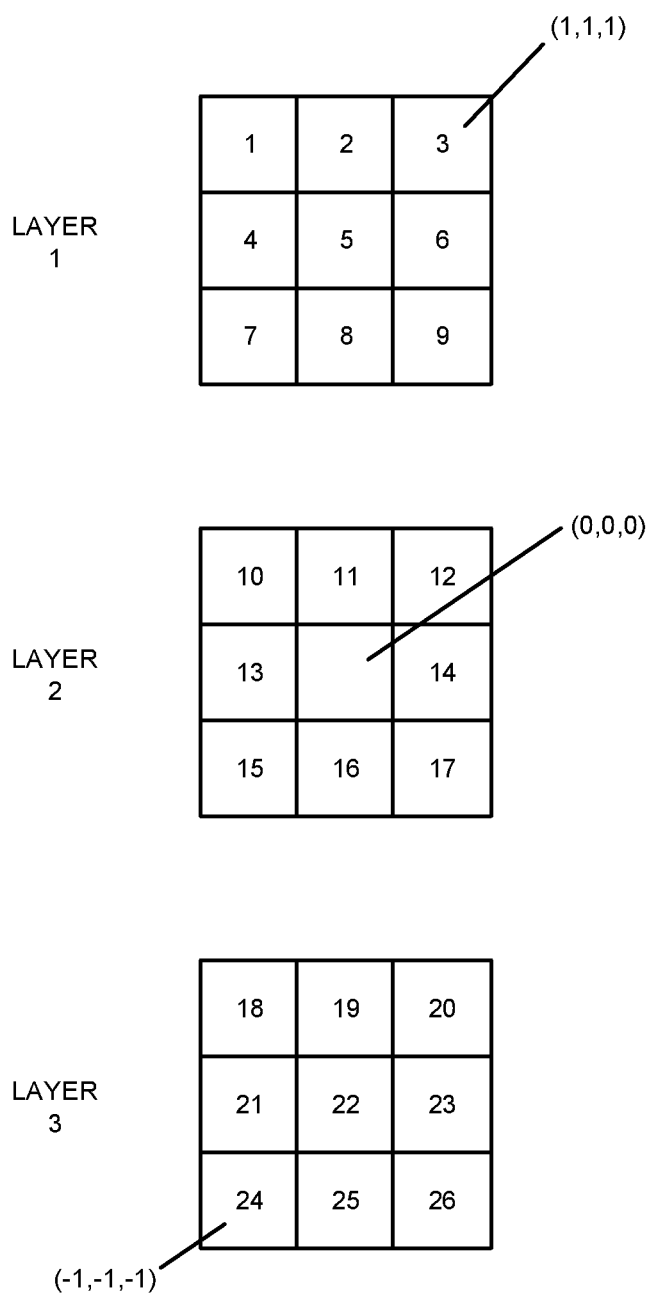
FIG. 3 is a drawing illustrating the determination of an MR model in accordance with an embodiment of the present disclosure.

As described further below with reference to FIG. 3, the measurements and recorded signals associated with MR scanner 110 may be used to generate an MR model of MR scanner 110 that accurately predicts MR signal evolution or response for a phantom having known properties over a range of parameters ($T_1$, $T_2$, proton density, off-resonances, environment, location, temperature, pulse sequences, etc.) using the Bloch equations, full Liouvillian computations or another simulation technique. In this way, the MR model may characterize MR scanner 110.

The predetermined characterization of MR scanner 110 can be used to transform a generic invariant MR signature into a machine-specific invariant MR signature associated with a particular MR scanner, such as MR scanner 110. In conjunction with the magnetic field and the pulse sequence, the machine-specific invariant MR signature may be used to predict or calculate simulated MR signals during an arbitrary MR scan in the particular MR scanner. Similarly, predetermined characterizations of different MR scanners can be used to convert from one machine-specific invariant MR signature to another.

In some embodiments, the predetermined characterization of MR scanner 110 includes measured ambient noise from electronics in or associated with MR scanner 110. During subsequent MR scans or simulations, digital filters may use the measured noise (or statistical parameters that describe the measured noise) to improve the quality of measured MR signals and/or calculated MR models. Moreover, the various measurements may be synchronized with an external reference clock or to a biological time period (such as a respiration period, a heart-beat period, a fundamental period for body motion, etc.) to enable subsequent synchronous averaging or additional signal processing.

Moreover, during the measurement technique, computer system 114 may repeatedly perform MR scans of different materials (such as different types nuclei) in individual 112 using MR scanner 110 based on instances of the scanning instructions that are received via network 130. Note that the MR scans of the different materials may be pseudorandomly acquired. For example, an MR scan of a particular material in individual 112 may be selected based on a random or a pseudorandom number provided by a circuit or software-implemented random or a pseudorandom number generator in computer system 114. Alternatively, the different materials in individual 112 may be systematically scanned for each instance of the scanning instructions.

Furthermore, the MR signals acquired or captured during a particular MR scan may be used to modify or adapt an MR model of voxels in individual 112. For example, as noted previously and as described further below with reference to FIG. 3, computer system 114 may determine the MR model (such as parameters in the MR model) based on differences (or a difference vector) between MR signals associated with the voxels in one or more MR scans and simulated or calculated MR signals (which may be generated using the MR model, an instance of the scanning instructions and optionally the characteristics of MR scanner 110). Note that the difference vector may be weighted based on a priori computed information to reduce the error, e.g., to obtain the smallest difference vector or the smallest difference vector measured across a set of weighted simulated MR signals (which may be precomputed). In some embodiments, the difference vector is determined using a dot product or inner product of one or more MR signals and simulated MR signals (which are each associated with or corrected to a common magnetic-field strength), cosine similarity between one or more MR signals and simulated MR signals, spectral analysis, and/or another comparison technique.

Then, based on the remaining differences (or the remaining difference vector) and/or one or more detected potential anomalies, the scanning instructions may be modified, i.e., a new instance of the scanning instructions (including one or more magnetic-field strengths and one or more pulse sequence(s) that will be applied to individual 112, the MR technique, the regions of interest in individual 112, the voxel sizes and/or the types of nuclei) may be determined. These operations may be iteratively repeated until a convergence criterion is achieved. For example, the convergence criterion may include that the difference between the MR signals and the simulated MR signals is less than a predefined value (such as 0.1, 1, 3, 5 or 10%) and/or that the changes to the scanning instructions are less than the predefined value. Furthermore, the convergence criterion may include completion of the scan plan.

As noted previously, these capabilities of the system 100 may allow scans to be performed as needed, after a time interval or periodically on an individual, so that the biovault can amass information and knowledge about the individual's (as well as other individuals) body and health. This information and knowledge can be used tailor or target scan plans based on the individual's needs, such as based on changes over time in their body.

Figure 2:
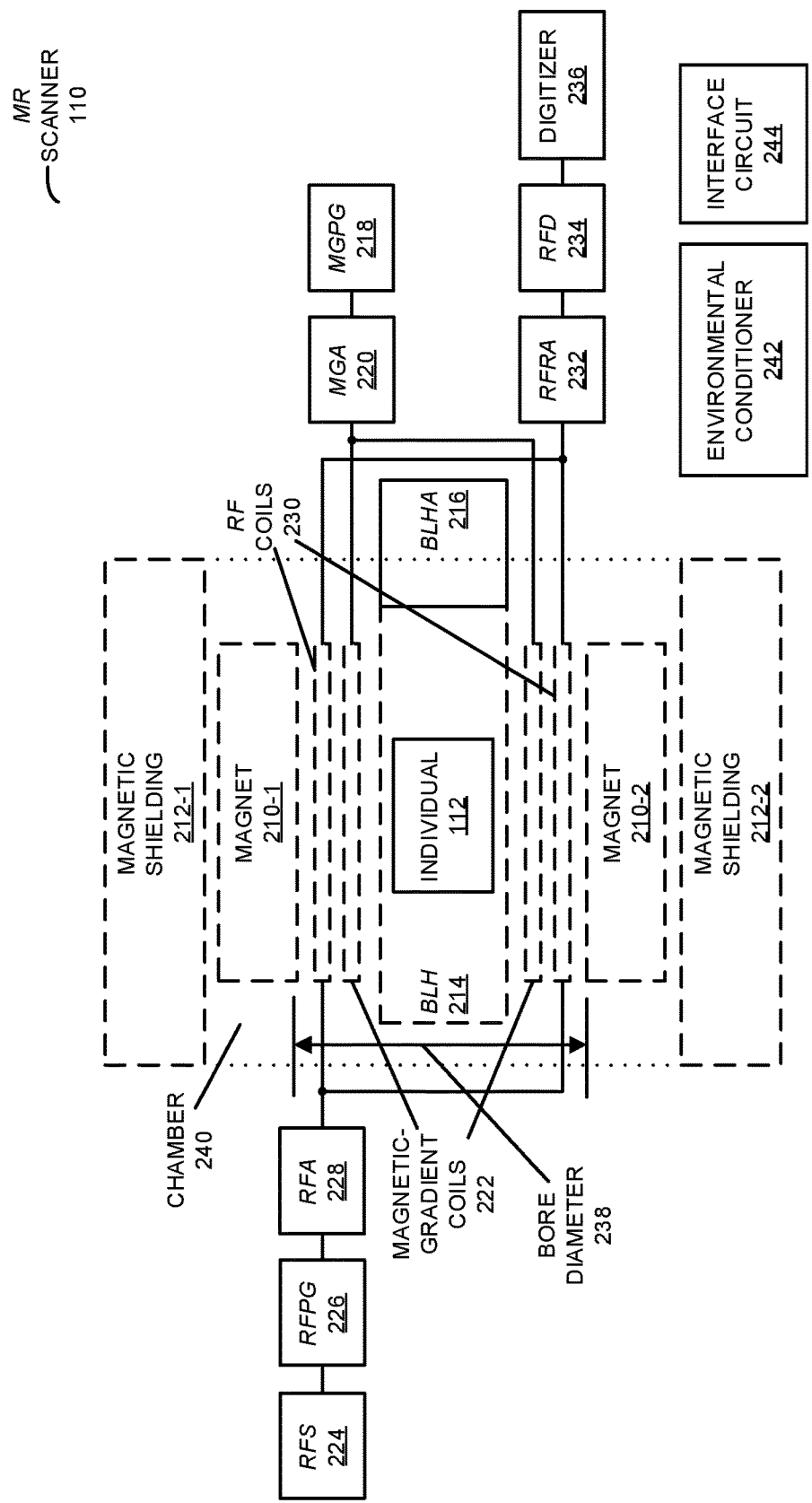
FIG. 2 is a block diagram of the MR scanner in the system of FIG. 1 in accordance with an embodiment of the present disclosure.

We now further describe operations in the measurement technique in more detail. FIG. 2 presents a block diagram of an example of MR scanner 110. This MR scanner may include a magnet 210, magnetic shielding 212, a biological lifeform holder (BLH) 214, a biological lifeform holder articulator (BLHA) 216, a magnetic-gradient pulse generator (MGPG) 218, a magnetic-gradient amplifier (MGA) 220, magnetic-gradient coils 222, an RE pulse generator (RFPG) 226, an RF source (RFS) 224, RF amplifier (RFA) 228, RF coils 230, an RF receive amplifier (RFRA) 232, an RF detector (RFD) 234, a digitizer 236 (such as an analog-to-digital converter), an environmental conditioner 242 and an interface circuit 244. (Note that mechanical and electrical connections to environmental conditioner 242 and interface circuit 244 are not shown in FIG. 2.) At least some of these components may be coupled, via interface circuit 244, network 130 (FIG. 1) and interface circuit 116 (FIG. 1), to computer system 114, which may control operation of MR scanner 110. The components in MR scanner 110 are described briefly below.

Note that MR scanner 110 may be a closed-bore or an open-bore system. In particular, magnet 210 (illustrated in a cross-sectional view in FIG. 2 by portions of magnet 210-1 and 210-2) may be closed bore or open bore. For example, a bore diameter 238 of magnet 210 may be between 1 and 10 cm or between 5 and 30 cm. An open-bore system may generate a magnetic field using two plates separated by a gap, and individual 112 may be exposed to (and nuclei in individual 112 may be polarized by) the magnetic field between the plates. Alternatively, a closed-bore system may have a toroidal shaped magnet 210, individual 112 may be moved through a hole in the center of the toroid (thus, using a strong field or high field to polarize nuclei in individual 112). Moreover, the orientation of magnet 210 may be horizontal (which is sometimes referred to as 'horizontal bore') so that individual 112 moves horizontally through the magnetic field, but can also be vertically oriented. In general, MR scanner 110 may scan individual 112 in various positions, including at different angles, orientations and perspectives (e.g., by adjusting biological lifeform holder articulator 216). (Thus, when MR scans are performed on individuals or animals, MR scanner 110 may allow measurements to be made while an individual is standing, sitting, laying down, positioned on their side or even in motion, such as walking on a treadmill.) Note that embodiments with a smaller bore diameter 238 may allow MR scanner 110 to be portable.

Depending on the MR technique, the magnetic-field strength $B_0$ of magnet 210 may be low field (e.g., an electromagnet having a peak magnetic-field strength that is less than 0.1 T, such as a magnetic-field strength as low as 0.001 T or even 0 T), a strong field (e.g., a ferro-magnet having a peak magnetic-field strength of around 0.5 T) or high field (e.g., a superconducting magnet having a peak magnetic-field strength greater than around 0.5 T). In general, a wide variety of magnets and magnetic configurations may be used. In embodiments with a superconductor, magnet 210 may be cooled using a cryogenic fluid, such as liquid helium or liquid helium in a surrounding dewar filled with liquid nitrogen or that is refrigerated. However, in other embodiments magnet 210 operates at or near room temperature. Furthermore, magnet 210 may be modular, such as a set of superconducting rings that each have a peak magnetic-field strength of 0.5 T and that can be added, removed or moved to create different magnetic-field magnitudes and configurations.

Magnet 210 may produce magnetic fields that can be changed physically and/or virtually (via gradient fields and/or pulse sequences). This capability may allow slow rotation of the main external magnetic field, so that MRS can be performed at low magnetic-fields strengths. This additional degree of freedom may provide more ways to perturb the magnetic moments in individual 112 to obtain information that can reduce the complexity of the invariant MR signature calculations. Note that moving or changing the orientation of magnet 210 may involve: moving pairs of ring magnets closer or further away on the z axis as part of a scan plan; rotating magnet 210 relative to the volume of space being indexed; changing the orientation/alignment of magnet 210 with respect to the z axis of the volume being indexed, etc. Moreover, 'physically' can mean physical movement of magnet 210, while 'virtually' may indicate that gradient fields and/or pulse sequences (such as a so-called 'spin-lock technique') are used to achieve the same result without physically changing the orientation of magnet 210. In general, these techniques may be used independently of each other or two or more of the techniques may be used in conjunction with each other.

Magnet 210 may also be used to (intentionally) dynamically vary the magnetic-field inhomogeneity. For example, by physically rotating a shim coil and/or by applying particular pulse sequences, the magnetic-field inhomogeneity may be modified. Moreover, by introducing specific kinds of magnetic-field inhomogeneity at different points in space, MR scanner 110 can differentiate certain kinds of tissue that are in close proximity.

Magnetic shielding 212 may include steel plates or metal sheets of silicon steel. This magnetic shielding may be placed all around a room, fully covering walls, floors and ceilings, in order to attenuate the magnetic-field strength outside the room to below 5 Gauss (or 0.5 mT). Moreover, special doors and doorframe seals may be used to further reduce the magnetic field that 'leaks' out of the room. Furthermore, magnet 210 may include shielding (such as a second set of superconducting windings with an opposite current flow than the main superconducting windings) in order to reduce the fringe magnetic field. For example, the magnetic-field strength may be 0.5 mT at a distance of four meters from magnet 210. This configuration may reduce the amount of magnetic shielding 212 or may eliminate the need for magnetic shielding 212 entirely.

In some embodiments, magnetic shielding 212 may provide a chamber 240 (defined by a surface of magnetic shielding 212), and this chamber may be optionally sealed so that at least a portion of individual 112 or a tissue sample being measured is at less than atmospheric pressure (i.e., a vacuum chamber) or may contain an inert gas (such as xenon) that can be pre-polarized to improve the MR imaging quality. (More generally, a solid, liquid or gas contrast agent may be used to improve the MR imaging quality.) In particular, environmental conditioner 242, such as a gas valve and a vacuum pump that are controlled by computer system 114, may be used to reduce the pressure in chamber 240. Alternatively, environmental conditioner 242 may include the gas valve and a gas tank that selectively allow (under control of computer system 114) the inert gas to flow into chamber 240. However, in other embodiments chamber 240 is defined by or provided by a surface of biological lifeform holder 214.

Note that magnetic-gradient pulse generator 218 may provide gradient pulses. These gradient pulses may be amplified by magnetic-gradient amplifier 220 to a level suitable for driving magnetic-gradient coils 222. Note that magnetic-gradient pulse generator 218 and magnetic-gradient amplifier 220 may be controlled by computer system 114 via an interface circuit 116 (FIG. 1), network 130 (FIG. 1)

and interface circuit 244. For example, computer system 114 may specify the types and shapes of magnetic pulses provided by magnetic-gradient pulse generator 218, and may specify the amplification or gain of magnetic-gradient amplifier 220.

Moreover, magnetic-gradient coils 222 may produce the shape and amplitude of the gradient magnetic field along the x, y and z axes (in a right-handed Cartesian coordinate system). Magnetic-gradient coils 222 typically operate at room temperature and may produce spatial gradients in the magnetic field $B_0$. For example, in a horizontal bore system, a gradient in the magnetic field $B_0$ along the z-axis or direction (i.e., parallel to a symmetry axis of the bore of magnet 210) may be achieved using an anti-Helmholtz coil, with current in each coil adding to or subtracting from the magnetic field $B_0$ to achieve the gradient. Furthermore, gradients along the x and y-axes may be generated or created using a pair coils having a 'FIG. 8' shape (which create gradients along their respective axes).

In some embodiments, magnetic-gradient coils 222 have gradients of 100 mT/m and have fast switching times (or slew rates) of 150 T/m/s, which may enable a slice thickness of 0.7 mm and a voxel resolution of 0.1 mm in 3D imaging. However, by using high frequencies (such as frequencies above approximately 100 kHz), slew rates higher than the current U.S. slew-rate limit of 200 T/m/s may be used. If magnet 210 produces a larger magnetic-field strength (such as 7 T), an isometric voxel resolution of 60 μm may be achieved.

Furthermore, RF pulse generator 226 may generate RF pulses based on carrier waves output by RF source 224 (such as sinewaves or RF pulses having desired fundamental frequencies based on a target type of nuclei and magnetic-field strength $B_0$), and RF amplifier 228 may increase the power of the RF pulses to be strong enough to drive RF coils 230 (e.g., increasing the power from milliWatts to kiloWatts). RF coils 230 may create a magnetic field $B_1$ that rotates the net magnetization of type of nuclei in individual 112 based on the pulse sequence. Note that RF pulse generator 226, RF source 224 and RF amplifier 228 may be controlled by computer system 114 via interface circuit 116 (FIG. 1), network 130 (FIG. 1) and interface circuit 244. For example, computer system 114 may specify the type or shape of pulse(s) output by RF pulse generator 226, the frequencies in the carrier frequencies or pulses provided by RF source 224 and/or the amplification or gain of RF amplifier 228.

In some embodiments, RF pulse generator 226 shapes the carrier waves or RF pulses into apodized sinc pulses, which may smooth discontinuities that can adversely affect the measurements and/or subsequent signal processing (such as a Fourier transform). Apodized sinc pulses may excite the spin states of the nuclei, and these excited spin states may decay and release a pulse of RF energy that is captured during acquisition. In general, a wide variety of pulse sequences may be used during the measurement technique. For example, the pulse sequence may include or may be associated with MR techniques such as: turbo field echo (TFE), fast field echo (FFE), susceptibility weighted imaging (SWE), short tau inversion recovery (STIR) or short $T_1$ inversion recovery (a type of suppression technique for fatty tissue with an inversion time TI equal to $T_1 \cdot \ln(2)$ so that the MR signal of fat is zero), turbo spin echo (TSE), fast low angle shot or FLASH (a type of spin-echo sequence in which larger tip angles provide more $T_1$-weighted images and smaller tip angles provide more $T_2$-weighted images), volumetric interpolated brain examination (VIBE), magnetic pulse rapid gradient echo (MP RAGE), fluid attenuation inverted recovery (FLAIR), a parallel imaging technique such as sensitivity encoding (SENSE), or another pulse sequence. Note that SENSE may involve: generating coil sensitivity maps, acquiring partial k-space MR data, reconstructing partial field of view images from each of RF coils 230, and combining the partial field of view images using matrix inversion. Moreover, the pulse sequence may include or may be associated with second and third generation parallel imaging techniques, such as GRAPPA, Auto-Smash or VD-SMASH, which are imaging techniques that speed up MRI pulse sequences using k-space undersampling, and the acquisition of additional lines provides a form of calibration because the coefficients of MR signals across RF coils 230 can be determined from the measurements. Furthermore, the pulse sequence(s) may be designed or selected to be independent of the hardware or MR scanner. For example, a pulse sequence may be designed or selected to cancel noise and amplify specific parameters of interest (which is sometimes referred to as 'quantum pumping'). (These pulse sequences may be used in NMR or MRI to quantify certain parameters in a machine-independent manner). As described below, quantum pumping may be used an alternative to pseudorandom pulse sequences.

Thus, in general, the pulse sequences may include: existing pulse sequences (when accurate measurements and simulations of the properties of the MR scanner can be obtained so that invariant MR signatures can be determined); pseudorandom pulse sequences (which may also involve accurate measurement and simulation of noise, but the pseudorandom nature may help to create more unique Bloch trajectories at each point in space); and/or quantum pumping (which may, at least in part, cancel out MR scanner-dependent noise, and thus, may simplify or reduce the required accuracy of the simulations used to determine the invariant MR signatures).

RF coils 230 also may detect the transverse magnetization as it precesses in the xy plane. In general, a given one of RF coils 230 may be transmit only, receive only or can transmit and receive RF signals. Moreover, RF coils 230 may be oriented such that the magnetic field $B_1$ is perpendicular to the magnetic field $B_0$. Furthermore, RF coils 230 may be tuned to the Larmor frequency (e.g., the resonant frequency of a type of nuclei being imaged or measured at the magnetic field $B_0$), e.g., by adjusting a capacitor or an inductor, or changing its capacitance or inductance (such as by using matching and tuning capacitors). Note that RF coils 230 may include: an Alderman-Grant coil, a bird cage (which may be used for volume measurements), a butterfly coil, a dome resonator, a gradiometer, an implantable coil, an inside out/Schlumberger coil, an intravascular coil, a ladder coil, a Litz coil, a loop-gap resonator coil, a loop-stick coil, a meanderline coil, a mouse coil, a multi-turn solenoid coil, a phased-array coil, a phased-array volume coil, a ribbonator coil, a saddle coil, a scroll coil, a single-turn solenoid coil (which may be used for extremity measurements), a spiral coil, a surface coil (which may be used for receiving body or volume signals because they have a good signal-to-noise ratio for tissues and samples adjacent to the coil), a multinuclear surface coil, a diffusion-tensor-imaging surface coil, a superconducting coil, a transmission-line coil, a truncated-spiral coil, a 3-axis coil, and/or a wide-band RF coil (which may be used to simultaneously excite multiple spectra). Note that coils with additional density can be designed to focus on regions of particular interest, such as: the brain, the abdomen, the chest, the reproductive, organs, spine, a joint (e.g., the neck, a shoulder, a knee, an elbow, a wrist, etc.), hands or feet. Moreover, the one or more of RF coils 230 may be full-body coils that are designed to capture the full body.

In some embodiments, one or more of RF coils 230 includes a thermal imaging sensor, which can include a forward looking infrared (FUR) sensor. (This may allow thermal imaging and MRI of, e.g., breast tissue.) Note that one or more sensors (such as the one or more of RF coils 230) in MR scanner 200 can be attached modularly (e.g., snapped together in concentric shells, snapped on additions, assembled with interlocking interfaces, etc.) and can communicate with each other via wireless or wired communication.

Furthermore, the one or more of RF coils 230 may be included in form-fitting elastic fabric that resembles football pads or suit of armor, and the size can be adjusted based on the size of individual 112. Additional RF coils can be included in hats, helmets, long-sleeve shirts, pants, gloves, socks, legwarmers, tights, jackets, vests, breeches, and/or other clothing items. For example, a measurement-equipped suit may include a soft wearable set of RF coils that is worn by individual 112, and then individual 112 can also be enclosed in a more rigid suit, such as a clamshell design. Note that the soft, wearable clothing suit may have one or more integrated ultrasonic generators attached to some or all parts of the body and/or integrated electrocardiogram sensors, and the harder outer shell may include integrated optical and thermal sensors. In some embodiments, a head coil includes: a mirror, a prism, a fiber-optic cable, a holographic display, a retinal projector, a projection screen, a stereo-projection screen, and/or another type of display for presenting visual information.

Moreover, in some embodiments surface coils that can be controlled by software on computer system 114 that executes the scan plan allow certain modalities or MR techniques to be turned on and off in real-time as the analysis of individual 112 progresses (such as during a second MR scan in response to detection of a potential anomaly, which is sometimes referred to as a 'drill down' protocol scan) For example, this approach may allow MRE to be performed on an anomaly, or a thermal image to be acquired of individual 112 or the surrounding region. Thus, if a potentially anomaly is detected in the individual's chest, the system may decide to send an ultrasonic wave through their chest during MRE of the potential anomaly and/or the surrounding region. In these embodiments, RF coils 230 can be constructed to include multiple sensors and data-collection equipment to facilitate specialized anomaly detection. Thus, RF coils 230 may be optimized for parallel collection of data using: MRF, MRT, MRS, MRE, multi-nuclear imaging of two or more nuclei (such as $^1$H, $^{23}$Na, $^{31}$P, $^{13}$C, $^{19}$F, $^{39}$K, $^{43}$Ca, etc.), diffusion-tensor imaging, N-channel scanning, magnetic-field relaxometry, etc.

In some embodiments, MR scanner 110 includes non-inductive sensing technologies in addition to or instead of RF coils 230, such as a magnetometer, a superconducting quantum interference device (SQUID), opto-electronics, etc. Note that non-inductive sensors may enable sweeping of the magnetic field generated by magnet 210 without requiring that RF coils 230 be tuned to different frequencies corresponding to the magnetic-field strengths.

The RF signals received by RF coils 230 may be amplified by RF receive amplifier 232 and detected using RF detector 234. In particular, RF detector 234 may capture or demodulate the RF signals to baseband. For example, RF detector 234 may measure MR signals in their simplest form, such as the free-induction decay of excited spin states, though it is possible to receive many more complicated pulse sequences. Computer system 114 may control RF detector 234 via interface circuit 116 (FIG. 1), network 130 (FIG. 1) and interface circuit 244. For example, computer system 114 may specify which MR (or RF) signals to capture.

Note that RF detector 234 may be a linear analog detector, a quadrature analog detector or a heterodyne receiver. Linear analog detectors may capture MR signals along one vector in the coordinate space (e.g., the magnetization along the x or y axis), and a quadrature analog detector may simultaneously capture MR signals along two vectors in the coordinate space (e.g., the magnetization along the x and they axis. In some embodiments, a linear analog detector includes a doubly balanced mixer, and a quadrature analog detector includes a pair of double balanced mixers, a pair of filters, a pair of amplifiers and a 90° phase shifter.

Furthermore, digitizer 236 may digitize the MR signals received by the RF detector 234. For example, digitizer 236 may use a 1 MHz sampling frequency. While this may oversample the MR signal, digital filtering (such as filtering using by multiplying by a bandpass filter in the frequency domain or convolving using a sinc function in the time domain) may be used to capture the desired frequencies and to remove higher frequency signals. In the process, the amount of data to be processed and stored by computer system 114 may be reduced to a more manageable level. However, in general, a variety of sampling frequencies greater than twice the Nyquist frequency may be used. For example, there may be up to 1000 samples per MR signal so that a frequency resolution of at least 500 Hz can be achieved. Computer system 114 may control digitizer 236 via interface circuit 116 (FIG. 1), network 130 (FIG. 1) and interface circuit 244. In particular, computer system 114 may specify the sampling rate and/or filter settings used by digitizer 236.

After digitizing, computer system 114 (FIG. 1) may perform a variety of digital signal processing (such as filtering, image processing, etc.), noise cancellation and transformation techniques (such as a discrete Fourier transform, a Z transform, a discrete cosine transform, data compression, etc.). In general, the MR signal may specified in the time domain and/or the frequency domain. Thus, in some embodiments, the MR signal is represented in k space.

In one embodiment, the readings from RF coils 230 are digitized within or just outside of the coil assembly and transmitted wirelessly to computer system 114 to avoid messy cable tangling, and without creating significant RF noise in the frequencies of interest. For example, the data may be transmitted to computer system 114 at lower or higher frequencies than the Larmor frequencies of targeted nuclei in individual 112, which may allow the data to be filtered to exclude noise artifacts. Furthermore, in some embodiments RF coils 230 are tuned to receive one or more frequencies. For example, depending on the spectra desired, a wide-band receiver coil can be used or a software or hardware-based tuner can be used to automatically tune at least one of RF detector 234 to receive one or more frequencies from a desired nuclei or molecule. (However, as noted previously, in other embodiments an un-tuned receiver, such as a magnetometer, is used.) Additionally, in embodiments where parallel imaging techniques are used, different parts of surface coils on individual 112 operate in parallel to concurrently or simultaneously capture different spectra.

Note that biological lifeform holder 214 may support individual 112 while individual 112 is moved through the magnetic fields and measured by MR scanner 110. Moreover, as noted previously, biological lifeform holder articulator 216 may articulate or move biological lifeform holder 214 as needed to position individual 112 in relation to the magnetic fields generated by magnet 210 and magnetic-gradient coils 222. In particular, biological lifeform holder articulator 216 may rotate individual 112 in 2D or 3D while individual 112 is being measured by MR scanner 110 based on instructions received from computer system 114 via interface circuit 116 (FIG. 1), network 130 (FIG. 1) and interface circuit 244. Furthermore, as noted previously, biological lifeform holder 214 may be enclosed in chamber 240 or may be an enclosed chamber, including a sealed chamber that can be pumped down to reduced pressure using a vacuum pump or flooded with an inert gas. In some embodiments, because environmental conditions can have an effect on individual 112, biological lifeform holder 214 includes sensors that measure temperature, humidity, pressure, another environmental condition, etc. inside the room, inside chamber 240 that contains biological lifeform holder 214, or inside biological lifeform holder 214.

In some embodiments, biological lifeform holder 214 includes a tube (or a vessel) and biological lifeform holder articulator 216 includes one or more air jets. These air jet(s) can be used to manipulate the position of individual 112. For example, the tube can be made of glass (such as optically clear or transparent glass), Teflon (which may be transparent at other frequencies of electromagnetic radiation), or another suitable material. Moreover, the tube may include features on its outer surface (such as a texture, fins or other features) that enable individual 112 to be articulated or manipulated into different positions using a gripping or interlocking interface to a motor or robotic arm, thereby allowing system 100 (FIG. 1) to re-orient individual 112 during the indexing or sample-measurement process.

Moreover, the tube may be inserted into a multi-axis magnet, such as a multi-axis magnet provided by Cryomagnetics, Inc. of Oak Ridge, Tenn. Then, system 100 (FIG. 1) can probe or measure individual 112 from multiple directions, angles, perspectives and alignments without requiring multiple sensors around bore 236. For example, individual 112 may be rotated, and a single camera, CCD or CMOS sensor can capture multiple photographs of individual 112 so that images of some or all of individual 112 may be captured, thereby reducing the cost and complexity of system 100, and improving the reliability. Furthermore, the tube may provide the chamber that is under vacuum or that is filled with an inert pre-polarized gas to increase the resolution. In some embodiments, a low-cost and portable chip-scale device (such as a microfluidic chip) is used to produce the polarized or magnetized gas, so that faint MR signals can be detected. For example, as noted previously, polarized xenon can be used as a contrast agent to enhance images in MRI of, e.g., human lungs. The polarized xenon atoms may be produced in the chip by collisions with rubidium atoms that are illuminated with circularly polarized light. Then, the polarized xenon may flow out of the chip and may be directed into the tube or chamber 240.

While not shown in FIG. 2, in some embodiments MR scanner 110 includes a watchdog or another automatic failsafe safeguard that monitors MR scanner 110. For example, the watchdog or automatic failsafe safeguard may monitor the specific absorption rate of individual 112 using thermal imaging. If a high or dangerous level of specific absorption is detected (such as one that may be perceived or that may cause pain or injury), computer system 114 (FIG. 1), via interface circuit 116 (FIG. 1), network 130 (FIG. 1) and interface circuit 244, may control pulse sequences to slow down or interrupt a current MR scan.

Referring back to FIG. 1, computer system 114 may instruct one or more optional measurement devices 124 to perform other measurements on individual 112 to obtain physical property information that specifies a measured physical property of individual 112, which may be used to determine a diagnostic classification of individual 112 and/or which may be included in metadata associated with individual 112. For example, the one or more optional measurement devices 124 may include: a medical grade scale that determines a weight of individual 112; a measurement device that measures one or more dimensions of individual 112 (such as: a laser imaging system, an optical imaging system, an infrared imaging system, and/or a spectroscopy system); a light source that can selectively illuminate individual 112 and a camera-enabled microscope that acquires or measures one or more optical images of individual 112 at one or more perspectives, orientations or lighting conditions; and/or a bioelectric impedance analyzer that performs a multi-lead measurement of an impedance of individual 112 at DC or an AC frequency (and which may correspond to hydration of individual 112, and thus may be used to determine or compute the hydration of individual 112). Alternatively, the hydration or hydration level, which can affect individual 112, and thus the invariant MR signature (and the MR signals), may be measured directly. In some embodiments, the other measurements on individual 112 include: cell cytology, genetic sequencing (such as sequencing some or all of the DNA in the genome, RNA sequencing or transcriptomics, gene expression, etc.), transcriptomics, protein analysis or proteomics (e.g., using mass spectrometry, metabolomics, liquid chromatography and/or NMR), epigenetic sequencing, lipidomics, microbiomics, radiomics, cytomics, toxomics (i.e., measurement of non-biological compounds in individual 112), an electrical measurement (such as an electrocardiogram, an electromyogram, an electroencephalogram, etc.), motion detection (such as body movement), acceleration, one or more vital signs, computed tomography, electron-spin resonance (which may be used to measure free radicals), x-ray imaging, ultrasonic imaging (e.g., ultrasound), photo-acoustic imaging, infrared imaging or infrared spectroscopy, other non-destructive measurements (such as radar or millimeter-wave scanning), activity or behavior data for an individual (such as data capture using a wearable electronic device), measurements performed by nano particles in individual 112, chemical composition of fluids (such as blood) measured at arbitrary locations in individual 112 non-destructively or by drawing a blood sample (e.g., using microfluidics), another quantitative or qualitative characteristic or property of individual 112, etc. Alternatively, computer system 114 may access data for some or all of these other measurements that are stored in a remote data structure (such as the biovault) based on the unique identifier for individual 112.

Note that the weight and the dimensions of individual 112 may be used to calculate their density. Moreover, the one or more optional measurement devices 124 may acquire images of individual cells for inspection and pathology identification. Furthermore, the medical grade scale may provide information about the chemical composition and hydration levels of individual 112 if individual 112 is weighed. The weight may be measured before and/or after the MR scanning (or other imaging operations). In some embodiments, measuring individual 112 in different portions of the electromagnetic spectrum may allow a correction for susceptibility artifacts that may not show in in optical or infrared scans, but that can occur in certain radio scans.

In some embodiments, system 100 includes an optional wave generator 126 that is controlled by computer system 114 via interface circuit 116. This optional wave generator may generate ultrasonic waves (and, more generally, mechanical waves) that are applied to individual 112 during MRE to measure a stiffness of individual 112. For example, optional generator 126 may generate waves at one or both ends of bore 236 (FIG. 2) of MR scanner 110 or may direct waves at one of both ends of bore 236 (FIG. 2) of MR scanner 110 using a waveguide, such that individual 112 receives the ultrasonic waves. In some embodiments, the ultrasonic waves include sheer waves. MR scanner 110 may acquire quantitative MR fingerprints or images of the propagation of the shear waves through individual 112, and may process the images of the shear waves to produce a quantitative mapping of the tissue stiffness.

(If, instead of an individual, a tissue sample that is embedded in formalin fixed-paraffin, then after the invariant MR signature is determined computer system 114 may transform the determined invariant MR signature so that it approximates an in-vivo tissue (i.e., without the formalin or the paraffin. For example, on a voxel-by-voxel basis, computer system 114 may subtract a predefined or predetermined invariant MR signature of the formalin or the paraffin from the determined invariant MR signature to generate an estimated invariant MR signature. Alternatively, computer system 114 may correct the parameters in the MR model on a voxel-by-voxel basis for the formalin or the paraffin to generate an estimated invariant MR signature. In some embodiments, a partial volume technique is used to subtract out the contribution or the effect of the paraffin or wax at borders of the tissue sample. In particular, computer system 114 may determine what percentage of a given voxel is paraffin and may remove or subtract out that weighted portion of the invariant MR signature or the MR signals that are used to computer the invariant MR signature.)

Furthermore, computer system 114 may store the raw data (such as MR signals from a biological sample or lifeform, the applied non-ideal pulse sequences, and measured noise), the invariant MR signature(s) and/or other measurements in the biovault, such as in memory 120 (which may be locally and/or remotely located, such as in a cloud-based archive device). In general, the measured information stored in the biovault may be sufficiently encompassing to allow the MR model to be trained based on the scanning instructions (e.g., using training engine 128) and, thus, the invariant MR signature(s) to be determined. Thus, the stored information may include different output signals at different points in the measurement pipeline (e.g., before an amplifier, after the amplifier, etc.), environmental conditions, geographic location, etc. The stored information may facilitate accurate simulations of an MR scan and individual 112, e.g., by training an MR model.

The stored information may include or may be associated with the unique identifier or a new unique identifier generated by computer system 114 that facilitates subsequent identification, as well as searching or querying of the biovault. Thus, if individual 112 is subsequently re-measured at a later time, computer system 114 may store the results or differential results (such as any changes in the invariant MR signatures) so that changes since the last measurements can also be used for searching. Moreover, the stored information may include information about the time, location and/or system parameters (such as information that specifies or identifies MR scanner 110) when individual 112 was measured. Note that the stored information may be encrypted. For example, symmetric or asymmetric encryption based on an encryption key associated with the unique identifier may be used.

In some embodiments, computer system 114 optionally compares the invariant MR signature of individual 112 to one or more other invariant MR signatures, which may have been previously determined for individual 112 or another individual. (Alternatively, computer system 114 may optionally compare a measured MR fingerprint or one calculated from or based on the determined invariant MR signature with one or more predetermined MR fingerprints. More generally, computer system 114 may optionally compare measured MR signals or those calculated from or based on the determined invariant MR signature with one or more predetermined MR signals.) Based on this comparison, computer system 114 may optionally determine a classification of individual 112 (such as a diagnosis), which may be stored in the biovault along with or associated with the unique identifier. Note that the determined or selected classification may be the one that has the lowest chance of being a classification error or the lowest matching error. Furthermore, if there are multiple potential or candidate classifications that have similar estimated classification errors (e.g., based on a predetermined supervised-learning model), then the classification of a given voxel may be determined based on a priori information, e.g., the classifications of nearby voxels or combinations (such as linear combinations) of these neighboring classifications, which may help reduce the classification error of the given voxel.

The ability to track labels or classifications and outcomes over time may allow the system to take an invariant MR signature and look up information that is known about it, such as: how frequently it is found, in which organs, has it been labeled bad or good, in which circumstances was it labeled bad or good, etc. In this way, the metadata about the MR signatures may get richer over time. For example, an individual (or tissue samples from the individual) may be indexed every six months. If cancer occurs during one of these indexing operations, this MR signature may be labeled 'bad.' But what about the classifications of historical MR signatures in that same region of individual 112? Does the cancer diagnosis potentially make them pre-cancerous? The system may find enough evidence, based on multiple MR scans, that the earlier MR signatures are early indictors of cancer and that there is a path through the MR-signature space is characteristic of this pathology evolving over time. Consequently, the biovault may allow such longitudinal and cross-individual analysis to identify such paths, which can be use in subsequent classifications and diagnoses, e.g., to detect one or more potential anomalies (such as a tumor).

Moreover, by comparing longitudinally for a particular individual and/or across individuals within the biovault, the system may be able to solve problems and assist in identifying pathologies without requiring the use of a deterministic machine-learning or supervised-learning model. For example, the system may be able to differentially identify the presence of a foreign object (such as screws, pins, joint replacements, etc.) embedded in individual 112 even if the biovault does not include or does not have previous knowledge about the foreign object. In particular, a ferromagnetic material may be detected based on the resulting magnetic-field distortion, and the invariant MR signature may include a correction for this magnetic-field distortion.

In some embodiments, the biovault provides the ability to aggregate invariant MR signatures on related individuals in other biovaults without these biovaults sharing other information about the individuals. This may allow global analytics to be performed on the individuals in siloed or isolated biovaults.

(If, instead of individual 112, a tissue sample is measured, system 100 may use an optional vacuum sealer to enclose and seal the tissue sample in vacuum in preparation for archival storage. Moreover, in some embodiments, the tissue sample is formalin fixed-paraffin embedded after the measurements. Furthermore, a physical or an electronic label may be attached to or associated with the tissue sample by an optional labeler to facilitate subsequent identification. The information in the physical or electronic label may include the information input and/or extracted at the start of the measurement technique. In some embodiments, the tissue sample is destroyed after measurements are made.)

While the preceding discussion illustrated the use of system 100 to scan or index individual 112, in other embodiments system 100 may be used to scan or index an individual or an animal multiple times, or multiple MR scans of different persons or animals. These scans may partially or fully overlap in time (i.e., may, at least in part, occur concurrently or simultaneously) to increase throughput.

Moreover, while the preceding discussion illustrated the technician or the MR operator using system 100, in other embodiments system 100 is highly automated, so that individual 112 may be loaded into MR scanner 110, MR measurements and/or the other measurements may be performed, one or more potential anomalies may be detected, an invariant MR signature can be determined, information may be stored in the biovault, individual 112 may be removed, and these operations can be repeated for one or more additional MR scans with minimal or no human action.

We now further describe determination of an invariant MR signature. FIG. 3 presents a drawing illustrating an example of determination of an MR model. The MR model may be a 3D model of voxels in a portion of an individual (and, more generally, a biological lifeform), and may include parameters in the Bloch equations for each of the voxels. In particular, with a quasi-static magnetic field $B_0$ along the z axis, the Bloch equations are $$\frac{dM_x(t)}{dt} = \gamma \cdot (\vec{M}(t) \otimes \vec{B}(t))_x - \frac{M_x(t)}{T_2},$$

$$\frac{dM_y(t)}{dt} = \gamma \cdot (\vec{M}(t) \otimes \vec{B}(t))_y - \frac{M_y(t)}{T_2}, \text{ and}$$

$$\frac{dM_z(t)}{dt} = \gamma \cdot (\vec{M}(t) \otimes \vec{B}(t))_z - \frac{M_z(t) - M_0}{T_1},$$

where $\gamma$ is the gyromagnetic ratio, $\otimes$ denotes a vector cross product and $\vec{B}(t)=(B_x(t), B_y(t), B_0+\Delta B_z(t))$ is the magnetic field experienced by a type of nuclei in the individual. The parameters in the Bloch equations may include $T_1$, $T_2$, a density of a type of nuclei, diffusion, velocity/flow, temperature, and magnetic susceptibility. Note that there may be different parameters for different types of nuclei for each of the voxels. Moreover, note that the Bloch equations are a semi-classical, macroscopic approximation to the dynamic response of the magnetic moments of the type of nuclei in the individual to a time-varying magnetic field. For example, there may be 67 M cells in a 1 mm$^3$ voxel.

In principle, the solution space for the parameters in the Bloch equations for the individual may be underdetermined, i.e., there may be significantly more parameters to be determined than there are observations with which to specify or constrain the parameters. Therefore, the measurement technique may leverage additional information to constrain or reduce the dimensionality of the problem. For example, an aspect of the anatomy of the individual may be determined using other imaging techniques, such as computed tomography, x-ray, ultrasound, etc. Moreover, tissue that does not look like (i.e., that has very different MR signals) than a targeted type of tissue (such as heart tissue) may be excluded from the MR model. Alternatively or additionally, tissue that deviates significantly from the expected MR signals based on previous MR scans (e.g., anomalies or changes) may become the focus of the MR model, such as by using a contour map (e.g., a cubic spline) to bound the regions (or specify a boundary of the regions) where there are significant differences. Alternatively or additionally, the error between measured MR signals and simulated MR signals may be represented using one or more level-set functions, and the boundaries of regions with errors exceeding a threshold value may be determined based on the intersection of a plane corresponding to the threshold value and the one or more level-set functions. In addition, by performing scans at different magnetic-field strengths $B_0$ (which may provide similar information to pseudorandom pulse sequences) using different pulse sequences and/or different MR techniques, the ratio of parameters to observations may be reduced, thereby simplifying the determination of the MR model.

For example, if a portion of the individual included one voxel, there may be 4-10 MR model parameters (which specify an invariant MR signature) that need to be determined for a particular type of tissue. If the voxel includes M types of tissue, there may be 4M-10M MR model parameters (which specify M invariant MR signatures) that need to be determined for the particular type of tissue. As the number of voxels increases, this can appear to be a daunting problem.

However, because different types of nuclei have different Larmor frequencies, the spatial distribution of the types of nuclei and their local concentrations may be determined from the measured MR signals. Then, a predefined anatomical template for the human body (or a portion of the human body), with associated initial parameters for an MR model, may be scaled to match the spatial distribution of the types of nuclei and their local concentrations.

Next, for a type of tissue (such as a particular organ), the MR model parameters may be iteratively refined as the size of the voxels is progressively decreased (and, thus, the number of voxels is increased). This analysis may be driven by the error between the measured MR signals and simulated MR signals using the MR model. Over time, the focus during the training will be on the residual regions with errors that are larger than a convergence criterion. For example, the parameters in the MR model may be trained based on measured MR signals at one magnetic-field strength and then the error may be determined based on the predictions of the MR model at another magnetic-field strength. Furthermore, note that initially the MR model may assume that there is no contribution or interaction between different voxels. However, as the error and the voxel size is reduced, subsequently such contributions and/or interactions may be included when training the MR model.

In order to facilitate this fitting or computational approach, the measurement technique may determine 'surface signatures,' as opposed to 1D signatures. For example, using measurements at multiple magnetic-field strengths or in the presence of known magnetic-field disturbances (such as rotation), a set of MR trajectories may be determined as 'fingerprints' that can be used to determine the invariant MR signature(s). Note that each MR trajectory may be defined by a magnetic-field function rather than a fixed magnetic-field strength.

In an exemplary embodiment, a simulation that is used to determine the MR model may be vertex/voxel centric. Using a physical model (such as a Bloch-equation-based model) running at each vertex, the system may 'apply' pulse sequences or disturbance to the physical model of the individual being scanned. For example, a message may be broadcast to the vertices that describe the disturbance in terms of physical laws. Each of the vertices may compute its predicted change in state and the resulting forces and energies, which are then relayed as messages to adjacent vertices about the forces and energies exported from that vertex. When all the vertices have generated a message, the message has been forwarded to the adjacent vertices and the state of the system has been updated, a time interval in the calculation may be complete. This approach can be generalized so that the message is forwarded to non-cyclical paths of length N (where N is an integer) radiating out from the vertex to improve the accuracy of the simulation.

Once the state has been updated, a computational technique can be run over the new computed state and then compared to the measured state. The error may be the difference between the predicted state and the measured state. As the computational technique is applied, the system may determine how to optimally assign the current state to each vertex in a way that reduces or minimizes the global error. Next, the system may choose a new set of perturbations for the system and may broadcast these as a new message to the vertices, as well as executing this disturbance physically on the individual being scanned. In this way, the system may provide real-time or near-real-time analysis and feedback during the measurement technique.

Thus, the inverse problem of determining the MR model parameters based on measured MR signals may be 'solved' by minimizing the error or difference between the measured MR signals and simulated MR signals that are generated based on the MR model, characteristics of the MR scanner (such as magnetic-field inhomogeneity) and the scanning instructions used to acquire the measured MR signals. In some embodiments, the inverse problem is solved using one or more computational techniques, including: a least-squares technique, a convex quadratic minimization technique, a steepest descents technique, a quasi-Newton technique, a simplex technique, a Levenberg-Marquardt technique, simulated annealing, a genetic technique, a graph-based technique, another optimization technique and/or Kalman filtering (or linear quadratic estimation).

Note that the inverse problem may be solved using dynamic programming. In particular, the problem may be divided up and performed by multiple computers in parallel, e.g., in a cloud-based computing system. For example, a particular thread may attempt to solve the inverse problem for particular scanning instructions. Multiple potential parameter solutions generated by the computers (or processors) may be combined (e.g., using linear superposition) to determine an error metric that is minimized using the one or more computational techniques.

Moreover, as described previously, the inverse problem may be solved iteratively by first attempting to find suitable parameters (e.g., parameters that minimize the error between the MR signals and simulated MR signals) for the MR model using a coarse voxel size and then progressively finding suitable parameters with smaller voxel sizes. Note that the final voxel size used in this iterative procedure may be determined based on the gyromagnetic ratio of a type of nuclei being scanned. The voxel size can also be determined based on the kind of 'query' that is made to the biovault or that forms the based on the MR scan plan, the current hardware configuration and/or hardware limitations. Furthermore, the voxel size or locations may also be chosen so that a voxel is evenly portioned into a set of subvoxels, or so that there is certain amount of overlap with preview voxel sizes to effectively oversample; the overlapping region and potentially further localize where an MR signal originates. As described further below, this last technique may be akin to shifting the entire gradient system in one or more dimensions by a distance dx that is less than a characteristic length of the voxels (such as a length, a width or a height of the voxels). In some embodiments, the voxel size in the MR model is smaller than that used in the MR scans (i.e., the MR model may use a super-resolution technique).

Additionally, the MR model may include simulations of dynamics, such as motion associated with: respiration, a heartbeat, blood flow, mechanical motion, etc. (Thus, there may be additional terms in the Bloch equations for diffusion, thermomemtry, spectroscopy, elastography, etc. Consequently, the MR model may be based on the Bloch-Torrey equations, etc.) For example, when a voxel contains a space that has a fluid flowing through it (such as in a vein), the flow of the liquid may be simulated by building a map of the flow directions and velocity magnitudes in the individual being scanned to be accounted for it the computation of the invariant MR signature. Furthermore, when scanning a human or an animal, the MR model may include the resting motion (such as that associated with respiration, a heartbeat, etc.). As noted previously, in order to facilitate calculation of the MR model, measured MR signals and/or other temporal measurements may be synchronized with or relative to a reference clock or a biological time period.

The MR model may be used to predict how the individual's body will respond to particular scanning instructions In particular, the MR model may be used to simulate or estimate the MR signals for a particular MR scanner having particular characteristics, for particular scanning instructions and/or for a particular individual (who has a medical history, previous MR scan results, etc.). Stated different, an invariant MR signature (which is based on the MR model) may be used to determine representations or projections (i.e., the MR signals) in particular contexts, such as based on the particular characteristics of the MR scanner, the particular scanning instructions and/or the particular individual.

Thus, the MR model may allow system 100 (FIG. 1) to perform active learning. In particular, the MR model may be iteratively fit or determined based on 'queries' generated by a learning system or a learning engine (which may be implemented in computer system 114 in FIG. 1). In particular, the queries generated by the learning engine may include different magnetic-field strengths $B_0$, different electromagnetic pulse sequences and/or different ultrasonic pulse sequences that are based on confidence intervals for parameters in the MR model. Consequently, the learning engine may use the measured MR signals in response to these queries to determine unknown parameters in the MR model and/or parameters having a poor accuracy (such as a confidence interval greater than 0.1 1, 5 or 10%). More generally, the adaptive learning performed by system 100 (FIG. 1) may be based on a wide variety of measurements, such as optical/infrared spectroscopy, x-ray, computed tomography, proton beam, photoacoustic, ultrasound, etc.

While the preceding discussion used the Bloch equations as an illustrative example, in other embodiments full Liouvillian computations (such as a Liouville supermatrix of interactions between two or more elements) or another simulation technique are used. Note that the MR signals computed or predicted using the MR model may be sampled at a rate equal to or higher than twice the Nyquist frequency of MR signals acquired during an MR scan.

In an exemplary embodiment, computer system 114 (FIG. 1) first approximates the parameters in the MR model and computes the error (or difference vector) between the measured MR signals and simulated MR signals based on this initial MR model. Note that when there are multiple candidate parameter solutions (having similar errors) to the inverse problem for a thread corresponding to particular scanning instructions, computer system 114 (FIG. 1) may keep the candidates (i.e., a unique parameter solution may not be identified at this point in the calculation). Alternatively, if there is no unique parameter solution within a desired error range (such as less than 50, 25, 10, 5 or 1%), the best (least-error) parameter solution may be kept. In addition, when there is no parameter solution within the desired error range, computer system 114 (FIG. 1) may modify the scanning instructions.

Moreover, computer system 114 (FIG. 1) may compute first and second derivatives along a surface(s) of parameter solutions in the individual. (In order to facilitate calculation of a derivative, note that the parameters may be represented using one or more level-set functions.) A set of voxels along the line where the first derivative is zero may be identified. This set of voxels may be fit using a cubic spline with a minimum error between the voxel positions and the cubic spline. This fitting operation may be repeated at all the boundaries in the parameter-solution space. Moreover, the largest continuous surface within the boundary defined by the cubic splines may be determined and the parameter-solution calculation may be repeated to determine a new continuous surface that is within the previous continuous surface. This generalized framework may minimize the error across intra-voxel volumes, thereby improving the agreement between the MR signals and the simulated MR signals based on the MR model.

We now describe embodiments of how to determine a distribution of types of tissue. Using MRF as an illustration, define a dictionary $D_{mrf}$ of measured time sampled MR trajectories (or vectors) for different types of tissue dj (for j=1 to n) such that a measured MR signal $y_{obv}$ for a voxel can be expressed as $$y_{obv} = \sum_{j=1}^{n} \alpha_j \cdot d_j + \varepsilon,$$

where $\alpha_j$ are normalized weights $$\left(\text{i.e., } \sum_{j=1}^{n} \alpha_j = 1\right)$$

and ε is an error (i.e., $\varepsilon=(y_j, \alpha_j)$, for j=1 to n. This may define an intra-voxel linear equation problem. A generalized inter-voxel problem may model a set of voxels (such as a cube with 27 voxels) as a graph G. As shown in FIG. 3, every voxel in the set may have 26 edges to eight adjacent voxels.

A parameter solution to the inverse problem may be defined as one that minimizes the error.

Consider the case of two adjacent voxels u and v. The intra-voxel linear equations $U_y$ and $V_y$ need to be solved at both u and v. There are several possible outcomes. First, $U_y$ and $V_y$ may have unique parameter solutions (where a 'unique parameter solution' may be a best fit to an existing MR model, i.e., with an error or difference vector that is less than a convergence criterion) and the analysis may be finished. Alternatively, $U_y$ may have a unique parameter solution but not $V_y$. It may be possible that the parameter solution for $U_y$ imposes a constraint on $V_y$ such that $V_y$ has a single parameter solution, in which case the analysis may be finished. However, neither $U_y$ and $V_y$ may have unique parameter solutions, in which case combining the systems of equations (i.e., effectively increasing the voxel size) may yield a unique parameter solution. Moreover, neither $U_y$ and $V_y$ may have any parameter solutions, in which case the intra-voxel problem cannot be solved without further constraints.

In the last case, it may be possible to look at an adjacent voxel w, i.e., series voxels u, v and w, with the corresponding intra-voxel linear equations $U_y$, $V_y$ and $W_y$ need to be solved at u, v and w. Note that the intra-voxel linear equations $V_y$ and $W_y$ reduce to the previous case. When the intra-voxel linear equations do not reduce to the previous case, this paring operation can be applied recursively until it does and then the intra-voxel linear equations can be solved as described previously.

In general, this computational technique may be isomorphic to the problem of fitting a 3D surface (or volume) to minimize the error. One challenge in this regard is that it assumes that all adjacent volumes have an equal effect on the parameter solution $\alpha_j$ that minimizes the error.

The minimization of the error may initially assume that there is no inter-voxel contribution (i.e., that the voxels are independent). Subsequently, inter-voxel contributions may be included. In particular, considering adjacent voxel volumes, there are two distinct classes. Volumes that share a surface and volumes that only share a 1D edge. The minimization function can be improved by weighting the error contribution at voxel u at the center of the relative coordinate system. If the effect on the error is proportional to $r^{-2}$ (where r is the distance between center points of voxels) and assuming 1 mm isotropic voxels in the weightings, the minimization or fitting problem with inter-voxel contributions can be expressed as $$\min(\text{error}(y(0, 0, 0),$$
$$\alpha(0, 0, 0) + \frac{1}{(1)^2} \sum_{k=1}^{m} \text{error}(y_k, \alpha_k) + \frac{1}{\left(\sqrt{2}\right)^2} \sum_{l=1}^{p} \text{error}(y_l, \alpha_l),$$

where the summation over k is for adjacent voxels sharing a common surface (i.e., (−1,0,0), (1,0,0), (0,−1,0), (0,1,0), (0,0,−1) and (0,0,1)) and the summation over l is for a remainder of adjacent voxels sharing a common edge. The assumption in the analysis is that the most difficult place to fit or determine parameter solutions is at discontinuities or interfaces between different tissues. Consequently, during the measurement technique, computer system 114 (FIG. 1) may solve these locations first and then may solve the remaining locations.

Alternatively, because the magnetic contribution from neighboring voxels is proportional to $r^2$, given a sphere of radius R from the center of a primary or central voxel in the minimization problem, surrounding voxels may be weighted based on the how much the sphere expands into the volume of the adjacent voxels (and, thus, based on how strong their inter-voxel contribution is estimated to be). For example, there may be three different weights that need to be assigned, including: a weight for voxels that share a 2D surface, a weight for voxels that share a 1D line, and a weight for voxels that share a 0D point. Because there may not be a uniform tissue distribution within each voxel, the weights may be dynamically adjusted to model different kinds of distributions inside each voxel in order find the distributions that minimize the error. This may provide the ability to identify multiple MR signatures within a single voxel for different types of tissue. Note that, as computational power increases, the accuracy of the predictive model may increase and the computational technique used to solve the minimization problem (and, thus, the inverse problem) may be modified.

Thus, in embodiments where the invariant MR signature of a voxel depends on the invariant MR signatures of surrounding or neighboring voxels, the invariant MR signature of a voxel may be computed using $2^{nd}$ or $N^{th}$-order effects. For example, if there are N $1^{st}$-order invariant MR signatures (where N is an integer), there may be as many as $N!/(N-27)!$ $2^{nd}$-order invariant MR signatures (if all the voxels interact with each other). In some embodiments, locality is used to simplify the inverse problem. In this way, an invariant MR signature may be generated by incorporating how the invariant MR signatures in adjacent voxels effect the invariant MR signature in a primary (central) or $1^{st}$-order voxel.

In some embodiments, a dithering technique is used to overcome the arbitrary locations of the voxels relative to the distribution of types of tissue in the body. In particular, there may be two or more types of tissue in a voxel because of the arbitrary voxel placement or the current voxel size. This may significantly change the MR model parameters for this voxel. This may suggest that there is more than one invariant MR signature needed for the voxel. As described previously, in order to confirm this, the voxels may be displaced by a distance dx (which is a fraction of the voxel length, width or height) and the MR model parameters may be determined again. In the processes, the tissue distribution may be determined. Consequently, this approach may effectively increase the spatial resolution in the analysis without changing the voxel size.

Figure 4:
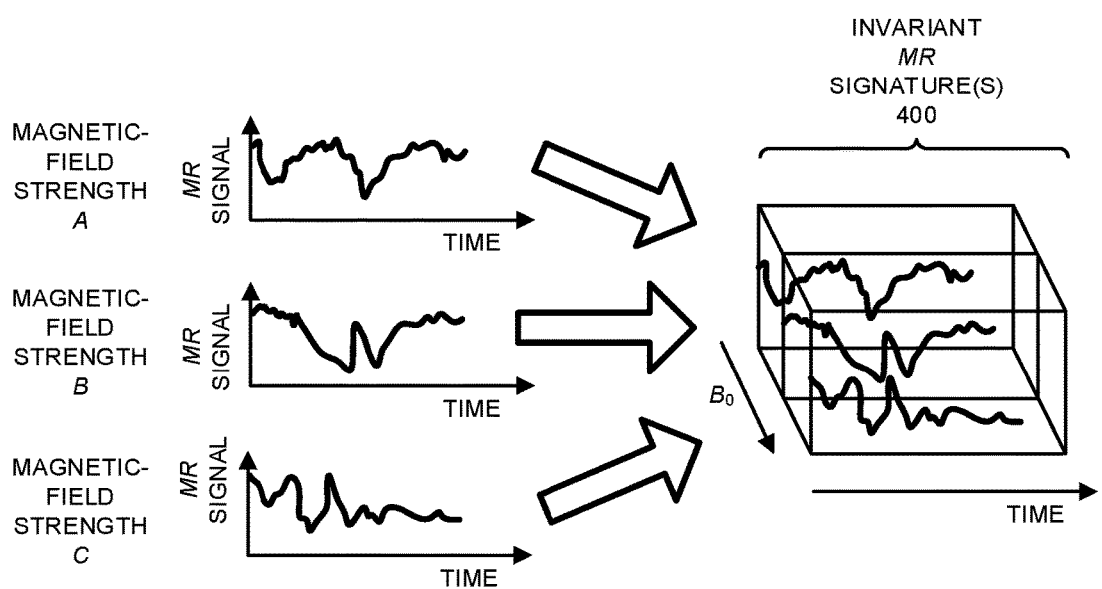
FIG. 4 is a drawing illustrating a set of MR signals that specify the response to a surface of magnetic-field strengths in accordance with an embodiment of the present disclosure.

FIG. 4 summarizes the preceding discussion of determining parameters for one or more MR models that accurately predict MR signals and their use in the biovault. In particular, MR signals or trajectories acquired at different magnetic-field strengths may be combined into a set of MR signals that specify the response to a surface of magnetic-field strengths. This response may be used to determine one or more invariant MR signatures 400.

Figure 5:
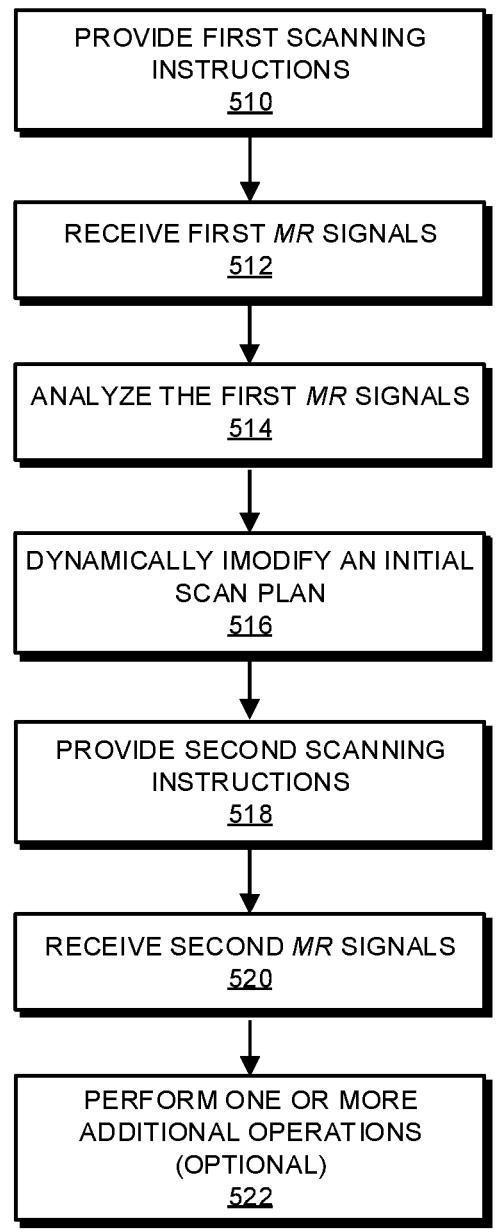
FIG. 5 is a flow diagram illustrating a method for performing an MR scan in accordance with an embodiment of the present disclosure.

We now further describe the method. FIG. 5 presents a flow diagram illustrating an example of a method 1000 for performing an MR scan, which may be performed by a system, such as system 100 (FIG. 1). During operation, the system may provide, to an MR scanner, first scanning instructions (operation 510) based on an initial scan plan to capture first MR signals of one or more first types of nuclei in at least the first portion of a biological lifeform, where the first MR signals are associated with first voxels having first sizes at first 3D positions in at least the first portion of the biological lifeform.

Then, the system may receive, from the MR scanner, the first MR signals (operation 512).

Moreover, the system may analyze the first MR signals (operation 514) to detect a potential anomaly in the first MR signals based on: a medical history of the biological lifeform; an MR-scan history of the biological lifeform that includes prior MR scans of the biological lifeform; and/or a first template of a potential anomaly (such as a multi-dimensional pattern or set of characteristics associated with the potential anomaly). Note that the first template of the potential anomaly may include simulated MR signals of the one or more first types of nuclei at the first voxels in at least the biological lifeform. In some embodiments, the system generates the simulated MR signals. For example, the generating of the simulated MR signals may involve: resampling predetermined MR signals; and/or interpolating the predetermined simulated MR signals at the first voxels. Alternatively or additionally, the simulated MR signals may be generated from a previously determined invariant MR signature, predetermined characteristics of the MR scanner and the initial scanning instructions.

Furthermore, the system may dynamically modify the initial scan plan (operation 516) based on the detected potential anomaly, the medical history and/or the MR-scan history, where the modified scan plan includes one or more second types of nuclei in second voxels, having associated second sizes, in at least a second portion of the biological lifeform, and where the second sizes are different than the first sizes. Note that at least the second portion of the biological lifeform may correspond to the 3D positions of the detected potential anomaly, and/or the second voxels sizes and at least the second portion of the biological lifeform may be computed from a size of the detected potential anomaly.

Additionally, the system may: provide, to the MR scanner, second scanning instructions (operation 518) based on the modified scan plan to capture second MR signals of the one or more second types of nuclei in at least the second portion of the biological lifeform, where the second MR signals are associated with the second voxels at second 3D positions in at least the second portion of the biological lifeform; and receive, from the MR scanner, the second MR signals (operation 520). Note that the second voxel sizes and at least the second portion of the biological lifeform may be based on a location in the biological lifeform of the potential anomaly.

In some embodiments, the system optionally performs one or more additional operations (operation 522). For example, the system may generate the initial scan plan for at least the first portion of the biological lifeform based on the medical history and the MR-scan history, where the initial scan plan may include the one or more first types of nuclei in the first voxels, having the first sizes, in at least the first portion of the biological lifeform. Moreover, the system may determine a recommended time for a subsequent MR scan of the biological lifeform based on one or more of: the medical history; the MR-scan history; and the detected potential anomaly.

Furthermore, the system may classify each of the voxels associated with the detected potential anomaly as having: a risk of misclassification that is less than a threshold value (such as 1, 5 or 10%); the risk misclassification that is greater than the threshold value; and/or the risk misclassification that is unknown. The system may: update, based on additional information (such as additional MR scans on the same or another biological lifeform, etc.) the classification; and change the recommended time for a subsequent MR scan based on the updated classification. For example, the system may use the analysis of a scan on another individual to modify the scan plan for the individual. In this way, as additional scans are performed and the learning in the system is adapted, this additional knowledge may be applied to other individual(s).

Additionally, the system may analyze the second MR signals to refine the detected potential anomaly based on one or more of: the medical history; the MR-scan history; and/or a second template of the potential anomaly (which may be the same as or different from the first template). Note that the second template of the potential anomaly may include simulated MR signals of the one or more second types of nuclei at the second voxels in at least the biological lifeform.

Note that the first MR signals may include a first MR image and the second MR signals may include a second MR image. Moreover, the second scanning instructions may correspond to: MRS, MRT, MRE, MRF, and diffusion-tensor imaging. Furthermore, the system may analyze adjacent voxels associated with the detected potential anomaly to determine a metabolic chemical signature in MRS.

Additionally, the analysis of the first MR signals (operation 514) may include instructions for aligning the first MR signals in the first voxels with anatomical landmarks of the biological lifeform in a prior MR scan of the biological lifeform and comparing the aligned first MR signals in the first voxels with prior first MR signals in the first voxels in the prior MR scan. For example, the aligning may involve performing point-set registration.

Note that the system may iterative perform, as needed, additional scans. Thus, the system may: provide, to the MR scanner, third scanning instructions based on the initial scan plan to capture third MR signals of the one or more first types of nuclei in a third portion of the biological lifeform, where the third MR signals are associated with the first voxels at third 3D positions in at least the third portion of the biological lifeform; and receive, from the MR scanner, the third MR signals, where the third MR signals complete the initial scan plan that was interrupted to capture the second MR signals.

Figure 6:
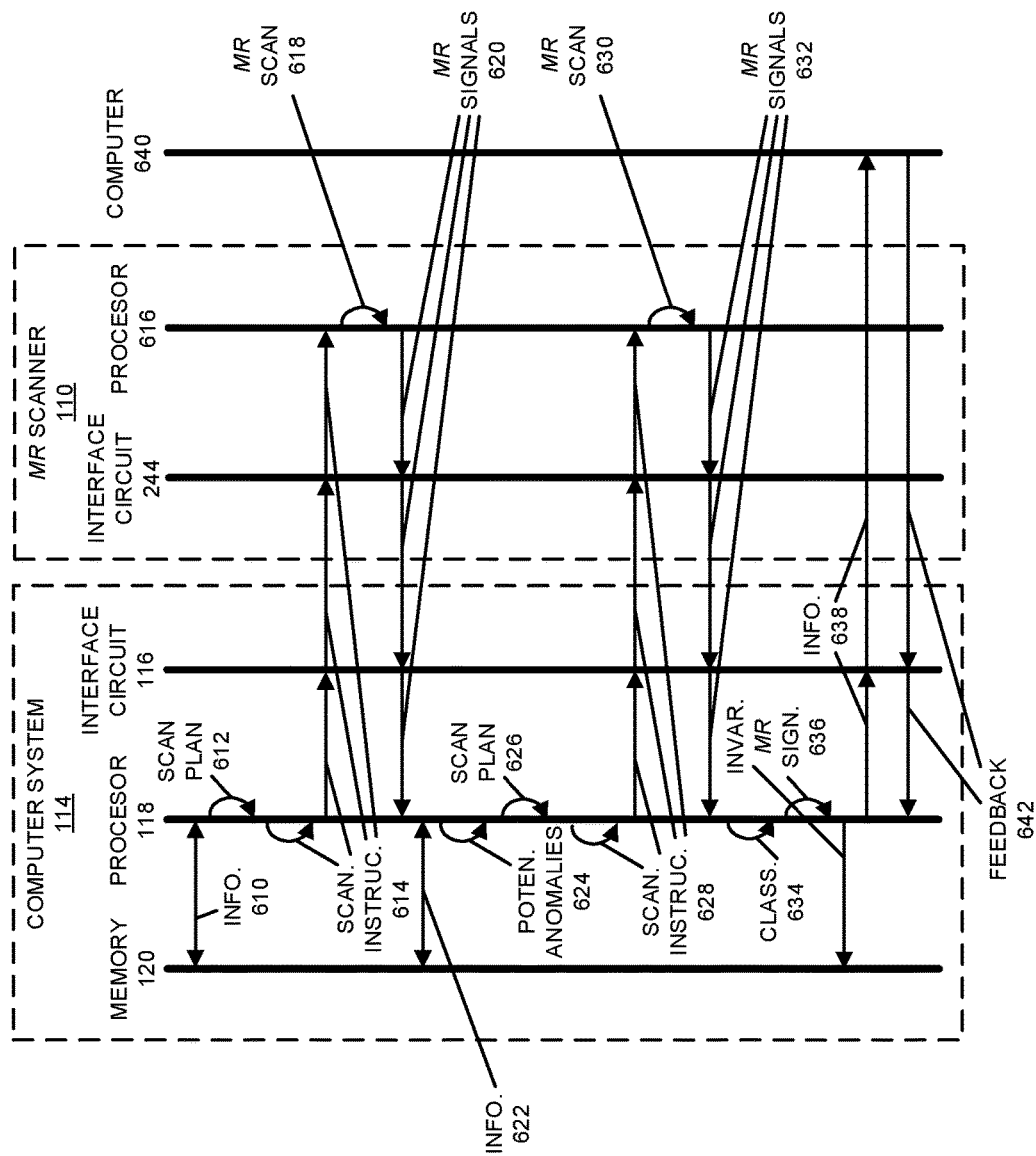
FIG. 6 is a drawing illustrating communication among components in the system in FIG. 1 in accordance with an embodiment of the present disclosure.

Embodiments of the measurement technique are further illustrated in FIG. 6, which presents a drawing illustrating communication among components in system 100 (FIG. 1). In particular, processor 118 in computer system 114 may access information 610 in memory 120. Using this information, processor 118 may determine a scan plan 612 and scanning instructions 614. Then, processor 118 may provide, via interface circuit 116, scanning instructions 614 to MR scanner 110.

After interface circuit 244 receives scanning instructions 614, processor 616 may execute them, so that MR scanner 110 performs an initial MR scan 618. During MR scan 618, MR scanner 110 may acquire or capture MR signals 620, which are provided to computer system 114.

Processor 118 may analyze MR signals 620 to detect one or more potential anomalies 624. This analysis may involve: registration, alignment, segmentation, simulation of MR signals, and/or comparison of MR signals 620 with one or more templates. During the analysis, processor 118 may access additional information 622 in memory 120.

Based on the one or more potential anomalies 624, processor 118 may dynamically update scan plan 626. Then, processor 118 may determine updated scanning instructions 628, which are provided to MR scanner 110.

After MR scanner 110 receives scanning instructions 628, processor 616 may execute them, so that MR scanner 110 performs MR scan 630. During MR scan 630, MR scanner 110 may acquire or capture MR signals 632, which are provided to computer system 114.

Note that processor 118 may repeat one or more of the aforementioned operations until the MR scan(s) of the individual are completed and/or a desired accuracy of one or more detected potential anomalies 624 is achieved. Furthermore, processor 118 may determine classification(s) 634 of one or more potential anomalies 624 and/or an invariant MR signature 636 based on the measured MR signals, which is stored in memory 620. Processor 118 may also store the MR signals, metadata and other related information in memory 620.

In addition, computer system 114 may provide information 638 about the MR scan(s) to a third party (such as a radiologist), such as to a computer 640 associated with the third party. Subsequently, computer 640 may provide feedback 642 from the third party that is used to update the current scan plan, a future scan plan, a recommended future scan time, one or more templates, etc.

In some embodiments of one or more of the preceding methods, there may be additional or fewer operations. Furthermore, the order of the operations may be changed, and/or two or more operations may be combined into a single operation.

In an exemplary embodiment, the system determines an initial scan plan. As described further below, the initial (as well as subsequent) scan plan may be based on information, such as: family history, personal medical history, previous scans, previously detected anomalies, previous medical lab test results (such as blood tests, biopsies and other tissue samples, urine tests, etc.), previous medical imaging results (x-rays, CT scans, ultrasound, etc.), previous scanning instructions (such as a recommended scan time), doctor's instructions (such as an instruction to scan the kidney), requests from an individual (such as a report of knee pain), information that specifies one or more risk factors for different pathologies, etc.

Because hydration can affect the quantitative MR scan results, the system may acquire additional information before a scan. For example, the system may measure a hydration level, can use a medical-grade scale and/or impedance measurements to determine a body-fat percentage.

The initial scan plan may indicate or specify a whole or full-body scan (head-to-toe) of individual. Based on the initial scan plan, the system may determine scanning instructions, such the 3D voxels. These voxels may be isometric and may have a size (such as 1 mm$^3$). In addition, the scanning instructions may specify spectroscopy of each voxel for types of nuclei including, but not limited to: $^1$H, $^2$H, $^{23}$Na, $^{31}$P, $^{14}$N, $^{13}$C, $^{19}$F, $^{39}$K, and/or $^{43}$Ca. However, these numerical values and types of nuclei are used as illustration, and other numerical values and/or types of nuclei may be used as technology improves or based on the abundance and gyromagnetic ratios of different types of nuclei. In particular, different voxels sizes may be used depending on the type of nuclei used, such as based on the region of the body and the pathology. Thus, the part of the individual's body being scanned can be an important factor in determining the voxel size(s) and/or the spectra chosen for imaging.

Figure 7:
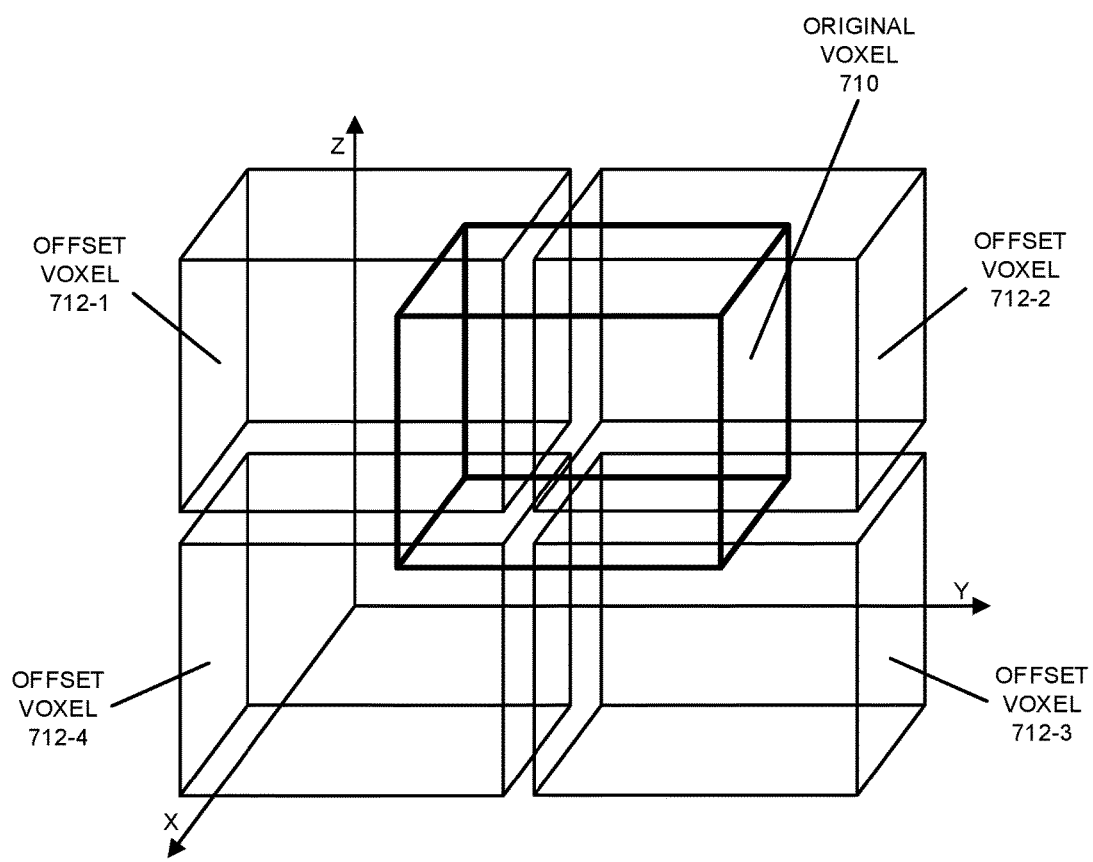
FIG. 7 is a drawing of a voxel and offset voxels illustrating an example of upsampling of individual voxels.

For example, some rare nuclei or nuclei that vary widely between parts of the body (e.g. calcium) can require a larger voxel size to get a strong enough signal with MRSI. As shown in FIG. 7, an original voxel 710 may be upsampled using measurements from offset voxels 712. Note that the front half of original voxel 710 (with respect to the y-z plane in Cartesian coordinates) is shown in the FIG. 7 (the rear half is not shown). Moreover, the upsampling may be arranged so as to divide original voxel 710 into eight regions that each overlap with eight of the offset voxels.

In FIG. 7, original voxel 710 is upsampled with 2× oversampling. However, other values of the upsampling rate may be used, such as 1.25×, 2×, 3×, 4×, 6×, 8×, etc. Furthermore, the offset voxels may be uniformly offset by half of the voxel size of original voxel 710 along each coordinate, or may be offset by variable amounts for each coordinate. While the voxels shown in FIG. 7 are isometric, in general the voxels may be non-isometric. For example, the voxels may have rectangular dimensions to capture patterns in MRS along a particular dimension, such as the spectra of glucoCEST molecules.

One advantage of upsampling is that it enables original voxel 710 to be compared (via addition, subtraction or other operations) to offset voxels 712 to create an interpolated map of the presence of rare nuclei that require larger voxel sizes. Upsampling can also enable chemical shifts, spin-spin interactions, and J-coupling to be reduced, filtered out, subtracted out or canceled out to reduce noise. For example, calcium may be detected in the heart using larger voxel sizes (because calcium occurs less frequently in healthy hearts). Then, multiple offset voxels can be captured for each voxel in the heart with a slight offset relative to the larger-sized voxels. The spectra in each original voxel and the relatively offset voxels may be averaged or subtracted from one another to interpolate a finer resolution picture of calcium in the heart, which can be indicative of the presence (or absence) of a calcified valve or another condition.

Similarly, in some embodiments, oversampling can be performed by capturing voxels of a particular size, and then capturing voxels of a smaller size within the same area. This may allow finer imaging of an area of interest or of a potential anomaly detected using a larger voxel size.

Depending on the desired information specified (directly or indirectly) in the initial scan plan, the system may include different types of nuclei in the scanning instructions. For example, the metabolites or properties that can be detected using $^1$H nuclei may include: total choline, lactate, lipid, N-acetyle-aspartate, citrate, extracellular pH (pHe), treatment efficacy, detection of metastasis, and tissue oxygen level ($pO_2$). Moreover, the metabolites or properties that can be detected using $^{19}$F nuclei may include: drug pharmacokinetics, pHe, $pO_2$, enzyme activity, and labeled-substrate utilization. Furthermore, the metabolites or properties that can be detected using $^{31}$P nuclei may include: energy metabolism (such as nucleoside diphosphates, phosphocreatine, or inorganic phosphate), intracellular pH (pHi), and phospholipid metabolism. Additionally, metabolites or properties that can be detected using $^{13}$C nuclei may include labeled substrate, such as drug pharmacokinetics and metabolic pathways. Note that the detection accuracy of $^1$H and $^{19}$F in MRS is typically within the millimolar range of the detected metabolite. In general, higher concentrations are typically required for less sensitive types of nuclei, such as $^{31}$P and $^{13}$C. In some embodiments, another type of nuclei is used, such as: $^7$Li, $^{14}$N, $^{15}$N, $^{17}$O, $^{27}$Al, $^{29}$Si, $^{57}$Fe, $^{63}$Cu, $^{67}$Zn, and/or $^{129}$Xe.

Moreover, the data captured for each voxel can include $T_1$-weighted images, $T_2$-weighted images, fat-suppressed images, diffusion-weighted images (which may measure the Brownian motion of water molecules in a voxel), and/or chemical-shift images to detect the chemicals that the nuclei are in (such as fat versus water).

Furthermore, contrast agents injected into an individual or a tissue sample can also be targeted for detection. For example, after an individual has been injected with a contrast agent (such as gadodiamide or gadobutrol), during an MR angiography scan (and using a moving table) a sequence of vessels may be scanned in order, including: supraaortal vessels, crural vessels, the thoracic/abdominal aorta, the abdominal aortal/iliac artery, the femoral/popliteal artery, etc. However, because of the improved resolution with stronger magnetic-field strengths (such as 3 T, 5 T, 7T, or larger), contrast agents may be less important and possibly unnecessary. Note that whole-body MR angiography can provide information about atherosclerosis, arterial stenosis, occlusion of arteries, and other vascular information.

Alternatively, more benign substances can be used as a contrast agent. For example, an individually may orally consume sugar (glucose) prior to a scan, and the metabolization of the glucose can be measured across tissues. Voxels of tissue that contain faster metabolic rates may be indicative of pathologies such as cancer, enabling the glucose to function as a contrast agent. When imaged, these metabolic rates can show tumors 'lighting up' or being illuminated and detected as potential anomalies or areas to monitor. In some embodiments, a non-injected contrast agent is used in an individual's lungs, nasal cavities or other air-filled cavities to allow 3D imaging. In particular, the individual may breathe a mixture of oxygen and helium. The helium can provide a stronger signal-to-noise ratio and may enable imaging of the lungs, nasal cavities or other air-filled cavities in the body. In another example of a contrast agent, nanoparticles of diamonds (e.g., diamond dust) can be administered to an individual (either orally or intravenously) to enable hyperpolarized $^{13}$C imaging.

As described previously, during the MR measurements based on the scanning instructions, a suit that contains surface coils and other measurement devices can be controlled by software executing the scanning instructions in the system, so that certain modalities can be turned off and on in real-time as needed. This capability may allow the scan plan to be modified in real-time based on data from the current scan, so that the system can collect additional information using the additional sensors, apparatuses and modalities.

For example, if a potential anomaly is detected in the chest, the system may decide to send an ultrasonic wave through the chest of an individual to take an MRE measurement of the potential anomaly or the surrounding region. In this example, the surface coils may include multiple sensors and data collection equipment that can be used for specialized anomaly detection. Thus, the suit may include sensors and RF coils that can be optimized for parallel collection of data in different measurements and MR techniques, such as: MRF, MRE, MRS, MRT, multi-nuclear imaging of two or more nuclei (such as $^1$H, $^{23}$Na, $^{31}$P, $^{13}$C, $^{19}$F, $^{39}$K and/or $^{43}$Ca), diffusion-tensor imaging, motion detection (e.g., using a thermal sensor or MRI imaging to capture motion of a body part, such as the hear, lung, a joint, etc.), heart-rate capture, electroencephalogram, and/or integrated EKG, optical and thermal sensors for motion detection, N-channel scanning, etc.

After acquisition of the MR signals, the system may perform signal-processing operations on the data to: reduce noise, improve the visibility of a particular scan (e.g., suppression processing), display the scan data on a display for an operator, analyze the scan data, perform segmentation on the scan data, register the scan data with historical scan data stored in memory, and/or another operation (such as determining an invariant MR signature). For example, the system may perform noise cancellation on received data. In particular, if an optical detector (such as a camera or an imaging sensor) captures motion (such as fine movements associated with breathing and/or heartbeats), the system can use this information to determine correction factors to the received data to reduce noise. Thus, when motion associated with a heartbeat is detected, the system may perform a transformation and may correct the MR signals (e.g., using a point-set registration between adjacent volume slices) to compensate for the detected heartbeat motion, to reduce artifacts and to provide improved image quality.

Then, the system may perform anomaly detection. As described further below, the system may compare MR signals (and/or one or more invariant MR signatures) from a current partial or complete scan against measured or simulated MR signals (based on one or more invariant MR signatures) for a historical scan, and may flag unexpected changes or changes that match predefined templates as potential anomalies. This may involve comparing registered and segmented portions of MR images to detect: changes in the size of segments or nodules/growths/swelling or other abnormalities, anomalies in MR spectrograms, anomalies in MR angiograms, anomalies in metabolic rates between adjacent voxels in a tissue, etc.

If no potential anomalies are detected in the current MR scan, the processing may end, and the scan results may be stored, e.g., in the biovault. Alternatively, if a potential anomaly is detected, the system may update the scan plan accordingly. In some embodiments, even if a potential anomaly is not detected, the system may update the scan plan based on feedback, such as from a radiologist and/or based on the results of MR scans of one or more other individuals in the biovault.

Based on the resulting updated scanning instructions, the system may perform a smaller, faster, more specialized or more targeted scan focused on the potential anomaly. The second MR scan may be a more detailed scan at a second set of voxel sizes (that are different from those used in the initial scan) to improve the visibility or detectable detail. Moreover, the second MR scan may focus on a different type of nuclei (e.g., nuclei having a different resonant frequency) and/or may use a different type of MR technique to determine more information about the potential anomaly.

For example, if a potential anomaly is detected in breast tissue based on the first (initial) scan, the potential anomaly could be a tumor, or it could be a small calcium cyst. The updated scan plan may seek to answer this question. Consequently, the second scanning instructions may look for particular metabolites using MRS to determine if the tissue outside of but proximate to the potential anomaly has a slower metabolic rate than the tissue inside the potential anomaly (which could indicate that the potential anomaly is a tumor). Alternatively or addition, the second scanning instructions may modify the MR frequency and may attempt to detect calcium nuclei within the potential anomaly to determine the likelihood that the potential anomaly is a calcium cyst.

As mentioned previously, in some embodiments the measurement technique uses breadth-first or dynamic indexing as a form of compressed sensing. Thus, different spatial resolution or voxel size (or a set of voxel sizes) may be used in different regions or in an initial or first MR scan versus a subsequent MR scan. (However, in some embodiments the same set of voxel sizes is used for the first scan and the second scan.)

We now provide some additional examples of in-depth scans that may be performed based on external conditions. In particular, when a patient reports knee pain, the scan plan may be updated so that system performs a second MR scan on either or both knees based on second scanning instructions that include a smaller voxel size than in a first scan to capture more information and higher-quality MRI images. Alternatively or additionally, the second MR scan may detect a different type of nuclei or may perform MRS to monitor the cartilage present in the knee(s).

Moreover, if a blood test indicates a malfunction or disease of the liver, the scan plan may be updated so that the second MR scan focuses on the liver with a smaller voxel size or performs MRS monitoring of metabolites in liver tissue. Furthermore, if a lesion is detected on the lymph node of an individual, the system may update the scan plan to collect more of the region around and including the lesion in the phosphorous spectrum to determine if the lesion is metabolizing faster that the surrounding tissue. The system may also perform diffusion-weighted imaging of the lesion, which could help to identify a malignancy. Additionally, if a lesion is detected in the breast of an individual, the system may update the scan plan to collect more of the region around and including the lesion in the calcium spectrum, because calcium deposits in breast tissue can be a precursor to breast cancer. The system may also perform imaging in the phosphorous spectrum to help to determine how the lesion is metabolizing with respect to the surrounding tissue.

In some embodiments, if an individual is overweight and a large amount of visceral fat is detected in the first scan, the scan plan may updated to perform a detailed scan of the pancreas to look for signs diabetes. Moreover, if calcification is detected on the aortic valve in the first scan, the scan plan may be updated to perform blood-flow analysis looking for a weakened vessel or a micro aneurism. Furthermore, if an anomalous difference in femur lengths is found in the first scan, the scan plan may be updated to perform a detailed scan of the individual's hip and knee cartilage in the sodium spectrum to look for signs of arthritis. Alternatively or additionally, if the system detects a rotation of the individual's pelvis within inflamed musculature in the first scan, in the second MR scan the system may look in more detail for structural issues in the individual's hip and/or spine.

Note that if the system detected white-matter lesions in the brain that can be an indicator of multiple sclerosis, the system perform a second MR scan at a different resolution or using spectra focused on the region containing the white-matter lesions in an attempt to identify justracoritcal lesions or other indicators of multiple sclerosis to differentiate against other pathologies that may be vascular or age related. The likelihood of one or the other pathology maybe indicated by additional data in the individual's medical history. For example, if the individual is very young, it may indicate a stronger need to do more detailed scanning rather than if the patient is very old and has no other symptoms of multiple sclerosis.

In another example, lesion detection in the prostate may rely heavily on functional imaging of the prostate and lesion staging may rely on high-spatial-resolution imaging of the prostate as well as a characterization of the remainder of the pelvis. Therefore, another region of the body (such as the pelvis) may be included in the second MR scan to aid in the lesion staging.

In some embodiments, flow-velocity mapping/modeling is followed by MRS to determine a kind of infarction. In particular, analysis of flow parameters in the MR model may allow an obstruction in a vessel to be identified. The location of an infarction in a blood vessel (such as an artery or a vein) may be determined without directly measuring the flow based on changes in blood flow velocities or parameters in the MR model that indicate increased blood pressure or turbulence. Moreover, based on Bernoulli's law, the narrowing of a blood vessel can be inferred without directly imaging plaque or a thrombosis. Then, the accuracy of this determination can be increased by performing MRS in the identified region to see if there has been an increase in the chemical signature expected from plaque buildup.

The MR signals acquired in the second MR scan may be processed using the same or similar signal-processing and analysis techniques as the MR signals from the first scan. If an additional potential anomaly is detected, the system may repeat at least some of the aforementioned operations and may perform a third scan. For example, if a second, fine-resolution scan of hydrogen nuclei (after the first scan of hydrogen nuclei) indicates that additional detail about a potential anomaly is needed, a third scan of sodium nuclei may be performed. Alternatively or additionally, MRS may be used to determine if a metabolite is present, or an MR angiogram may be used to confirm potential anomalies in blood-vessel walls. Therefore, at least some of the operations in the measurement technique may be repeated as addition potential anomalies are detected and/or when addition information related to a potential anomaly is needed. In some embodiments, a cycle-detection mechanism or module prevents the system from repeatedly detecting the same potential anomaly and/or repeatedly updating the MR scan plan, e.g., preventing an infinitely recursive loop.

In these ways, the system may iteratively detect and classify potential anomalies in the individual. Note that the potential anomaly and/or an additional potential anomaly may be highlighted for review by a physician, a radiologist and/or other healthcare provider or specialist.

In some embodiments, instead of or in addition to updating the current scan plan, the system updates a future scan plan, determines a recommended future scan time (or a return date for the individual) and/or sends out a calendar invite or another notification to the individual. For example, the objectives of the future scan plan and/or the recommended scan time may be based on analysis of an individual's risk factors (such as a determined risk score) for one or more pathologies and any anomalies that were detected. In particular, an individual with a detected anomaly may be instructed to return within a month or six months for their next scan. Alternatively, the future scan may be scheduled for 30 minutes after the completion of the current scan, and the individual may be instructed to consume chocolate to prime the individual's body with glucose before a scan focusing on metabolites 30 minutes later. The future scan plan may also include looking for additional anomalies highlighted for review by a physician, a radiologist or another healthcare profession. Furthermore, the scheduling of the future scan time (i.e., the recommended scan time) may be based on the availability of the MR scanner, the individual's personal schedule/calendar and/or one or more healthcare professionals' schedule/calendar.

Moreover, after the MR scan(s) and analysis are completed, the system may generate a summary report about the individual's health, including the most recently collected data, as well as some or all of the historical data. These reports can include suggested follow-up actions, such as, when the patient should return for a follow-up visit (such as the recommended scan time) or a recommendation to see a medical specialist to further review the data collected about a potential anomaly. For example, if the system detected a cardiac anomaly, such as calcification of the aortic valve, the system may recommend seeing a cardiologist. These recommendations may be mediated by a human operator, a healthcare professional (such as a physician), a user interface displayed on a display and/or via a mobile application.

The summary report may also compare the individual health and MR scan data to a larger population, such as the relative brain mass for the individual compared to other individuals of the same age, gender and body mass. Alternatively or additionally, the system may report that the amount of fatty tissue in and around the individual's liver has steadily increased over time and indicate the associated risks, as well as things the individual can do to reduce visceral fat in the body. Moreover, the summary report may indicate increases or decreases in lean muscle mass in certain muscles, a list of pathologies for which the individual is statistically at risk and actions that can be taken to reduce these risks. Thus, in the case of the cardiac anomaly, if calcification of the aortic valve is detected, the system may recommend a specific cardiologist or a list of cardiologists (such as cardiologists in the area, who are closest, who are available, who have the lowest cost, who are the highest rated, etc.). In some embodiments, with approval from the individual, the system may schedule an appointment and/or share relevant data that has been collected with the cardiologist.

As noted previously, in some embodiments, the first or initial MR scan is paused in response to an interrupt from the system when a potential anomaly is detected. In order to facilitate subsequent completion of the first MR scan, the position (which is sometimes referred to as the 'position context') in the first MR scan may be saved in memory for subsequent use. In addition, the scanning context of the MR scanner may be saved in memory for subsequent use. The scanning context of the MR scanner may include: a table or biological-lifeform holder position, magnetic-gradient pulse generator settings, RF sources, RF-source frequency settings, RF pulse-generator settings, and other MR-scanner configuration information. Note that the MR scanner may have to pause between the first MR scan and the second MR scan and, optionally, between the MR scan and a resumed first MR scan to wait for the magnetic-relaxation times (such as $T_1$, $T_2$, and the adjusted spin-spin relaxation time $T_2^*$) to decay to an appropriate level to allow spins to re-magnetize to the external magnetic field.

In these ways, the system may perform more-detailed scans (e.g., finer voxels or larger voxels targeting a different type of nuclei) or additional types of scans (MR angiography, MRS, etc.) in the middle of a larger scan, such as a general body scan or a general area scan. For example, if an individual has an involuntary episode (such as seizure, spasm, etc.) during an MR scan, the MR scan can capture information from the brain during the seizure. Information about muscle spasms, blood clots, seizures (epilepsy) can also be captured by saving the position and/or the scanning context immediately upon detection of an involuntary episode, and a second MR scan may be performed to capture information about the involuntary episode.

Furthermore, the system may incorporate and/or control treatment therapies that can be applied to a detected anomalies.

We now describe radiologist feedback in more detail. After an MR scan is completed, while an MR scan is being performed, and/or when a potential anomaly is detected, the system may provide information about the potential anomaly, associated metadata and/or related medical information to one or more radiologists (or other healthcare professionals) for evaluation, so that the one or more radiologists (or the other healthcare professionals) can confirm or correct the identification and the classification of the potential anomaly (and, more generally, can provide feedback, which is sometimes referred to as 'radiologist feedback'), and can provide instructions (if any) for a future scan plan or a future scan. For example, the information about the potential anomaly, the associated metadata and/or the related medical information can be provided and the feedback can be received using a distributed consulting software application or service. Note that a potential anomaly may be converted or re-labeled as an anomaly after it is reviewed by a radiologist. However, in some embodiments, the system may automatically determine if a potential anomaly is, in fact, an anomaly.

The radiologist feedback may be used to update the scan plan and/or when determining the future scan plan. In addition, the radiologist feedback may be used to update the anomaly detection, such as the templates or look-up tables used and/or the pathology information included in the biovault. For example, the changes to the templates, the look-up tables, and/or the pathology information may affect analysis of voxels associated with a portion of the body, a type of tissue, across historical scans for an individual, a group of similar or related individuals and/or the entire population of individuals captured by one or more MR scanners.

In particular, based on the radiologist feedback, the risk level for look-up table values for voxels characterized as unknown risk may be changed, the confidence of low-risk and high-risk values in a look-up table may be verified, reinforced, made more robust, or otherwise corrected or improved across at least a subset of the population in the biovault. For example, a radiologist may rate the stage of cancer in a detected potential anomaly in an individual's liver, and the look-up table values may be updated or otherwise verified for the individual, as well as similar individuals and/or the entire population of individuals scanned by one or more MR scanners.

In addition, the look-up table values and/or the pathology information included in the biovault may be updated based on information from research publications. This publication information may be entered manually or automatically by crawling newly released research papers using a document crawler or using another learning-software technique. For example, a new research paper highlighting a detection of a pathology based on metabolic rates in a type of tissue can be incorporated to update or reinforce a global anomaly detection technique (such as software, a program module or an engine). Then, the anomaly detection technique may be used to generate a look-up table that is used in the analysis to detect variation in metabolic rates for voxels in a type of tissue, and the improvement can be applied to some or all of the individuals that are monitored using the system. In some embodiments, the updated anomaly detection technique is applied retroactively to some or all of the existing or historical MR scans in the biovault. In this way, additional anomalies can be detected and the future scan plans for individuals with newly detected anomalies can be updated, which can result in the scheduling of additional scans, changing the scheduling of existing scans, as well as other medical responses (such as additional biopsies, medical lab tests, etc.).

We now describe the registration and segmentation operations in more detail. During a scan and/or the subsequent analysis, the system may perform registration and segmentation of MR signals. These operations on the acquired or captured MR signals (or the corresponding invariant MR signature(s)) may be facilitated by comparisons with historical data in the biovault, which may include registration and segmentation information from previous computations. Note that the registration between one or more MR images (either current and/or historic) can be performed using a wide variety of registration techniques, such as point-set registration.

In some embodiments, in order to use the previous invariant MR signature to generate the estimated or simulated MR signals, a registration technique is used to align the individual (or MR signals acquired for the individual) with reference markers at known spatial locations or with the voxels in the previous invariant MR signature. This registration technique may use a global or a local positioning system to determine changes in the position of the individual relative to an MR scanner.

Moreover, the previous invariant MR signature or estimated MR signals based on the previous invariant MR signature may be used during virtual registration of the individual. In particular, the previous invariant MR signature may be used to generate estimated MR signals for sets of voxels. The estimated MR signals in a given set of voxels may be averaged, and the resulting average MR signals in the sets of voxels may be compared to MR signals measured during a current scan to determine a static (or a dynamic) offset vector. For example, the positions of the average MR signals in the set of voxels (such as average MR signals in 3, 6, 12 or 24 regions or portions of an individual) may be correlated (in 2D or 3D) with the MR signals in the set of voxels in the current scan. This offset vector may be used to align the MR signals and the estimated MR signals during subsequent comparisons or analysis. Alternatively, the comparisons may be made on a voxel-by-voxel basis without averaging. Thus, the MR signals for a voxel in the individual may be compared to corresponding MR signals for the voxel measured on a prior occasion by performing a look-up in a table. In some embodiments, the registration or the offset vector of an individual is computed based on variation in the Larmor frequency and the predetermined spatial inhomogeneity or variation in the magnetic field of an MR scanner.

Furthermore, the registration technique may involve detecting the edges in node/voxel configurations. Because of the variability of anatomy across different individuals, transforming small variations of data into more generalized coordinates may be used to enable analysis and to generalize the results to a population. In general, the transforms may be one-to-one and invertible, and may preserve properties useful for identification and diagnostics, such as: curves, surfaces, textures and/or other features. For example, the features may be constrained to diffeomorphic transformations (such as smooth invertible transformations having a smooth inverse) or deformation metric mappings computed via geodesic flows of diffeomorphisms. In some embodiments, a diffeomorphic transformation between surfaces is used to compute changes on multi-dimensional structures (e.g., as a function of time).

Additionally, linear combinations of diffeomorphic transformations computed based on sets of matches between MR signals and simulated MR signals associated with one or more invariant MR signatures (or linear combinations of invariant MR signatures) can provide spatial offset corrections based on a piori estimated information (such as motion, deformation, variations in anatomy, magnetic field, environmental conditions, etc.). These spatial offset corrections may be used as a weighted component in a supervised-learning registration engine. For example, a set of diffeomorphic velocity fields tracking a set of points across a set of phases of distortion (caused by movement of the lungs during regular breathing, the heart during heartbeat motion or a muscle during contraction or expansion) can be applied to a region of the body corresponding to the sets of points in the region (e.g., a set of voxels in or around the heart or lungs).

Note that registration, segmentation and/or anomaly detection can be performed sequentially (e.g., in a pipeline) and/or in parallel.

We now describe anomaly detection in more detail. The system may detect discrepancies between the current MR scan and one or more historical MR scans. For example, the system may compare MR signals (and/or one or more invariant MR signatures) from a current partial or complete scan against measured or simulated MR signals (based on one or more invariant MR signatures) for a historical MR scan, and may flag unexpected changes or changes that match predefined templates as potential anomalies. As noted previously, this may involve comparing registered and segmented portions of MR images to detect: changes in the size of segments or nodules/growths/swelling or other abnormalities, anomalies in MR spectrograms, anomalies in MR angiograms, anomalies in metabolic rates between adjacent voxels in a tissue, etc.

For example, the segmented images can include images of the heart, and if a recent MR image includes a larger heart muscle than a historical MR image, an enlarged heart may be detected as an anomaly. A more in-depth scan may be requested in an updated scan plan at a smaller voxel size, and/or additional MR scans may be performed using MR angiography, MR colonoscopy, MR venography and/or MRS to provide additional information for use by a healthcare professional and/or for use in automated diagnosis by the system.

In another example, a first MR scan may include an image of a colon. If a polyp larger than approximately 8 mm is detected, which was either new or larger than in a previous MR scans, a finer resolution scan with a smaller voxel size may be performed to evaluate a potential colonic carcinoma. Alternatively, if the system detects a decrease in bone density over time in an individual complaining of hip pain, the system may image the hip region in greater detail to look for osteoporosis or fractures.

More generally, during the analysis the system may use an anomaly detection technique (such as a supervised-learning technique, comparisons with a previous MR scan data or information derived from a previous MR scan data, e.g., comparisons with values in a look-up table, comparisons with a template, e.g., a target pattern or set of characteristics that matches a particular pathology, etc.) to identify potential anomalies and/or pathologies. For example, the system may detect a potential anomaly by comparing an output of the anomaly detection technique with a disease-specific threshold or spatial pattern. Note that the anomaly detection technique may be trained using information that specifies risk factors, historical MR scan data, statistics (e.g., a mean, a median, a mode, standard-deviation outliers, etc.) associated with MR signals for voxels in one or more individuals, pathologies in the biovault and/or radiologist feedback.

Thus, during the anomaly detection, the system may flag unexpected changes as potential anomalies, e.g., by comparing registered and segmented portions of MR images to detect changes in the size of segments or nodules, growths, swelling or other abnormalities, detecting anomalies in MR spectrograms, detecting anomalies in MR angiograms, detecting anomalies in metabolic rates between adjacent voxels in a tissue, etc.

In some embodiments, the anomaly detection involves receiving historical MR scan data, and computing a look-up table for the voxels in the historical MR scan data. Then, the system may register 3D image slices of voxels for a current MR scan, and may compare at least one voxel from the 3D slice of voxels for the current MR scan with the corresponding entry in the look-up table for those voxels. Based on the comparison (such as based on a threshold), the system may classify the voxel as a low-risk voxel, a high-risk voxel, or as a voxel having an unknown risk. Alternatively, if the voxel is determined to be cancer, the voxel may be classified as an early-stage cancer voxel, a later-stage cancer voxel, or an unknown-stage cancer voxel. Note that an unknown-risk voxel or an unknown-stage cancer voxel may be flagged for review by a radiologist or for biopsy. Moreover, low-risk voxels and high-risk voxels may also be reviewed and verified by a radiologist or flagged for biopsy, but the classification can help the radiologist classify and evaluate images faster and more effectively.

As noted previously, if a potential anomaly is detected, the system may update the MR scan plan and the scanning instructions to include smaller, faster, more specialized or more targeted scans, scan lines, or partial scans focused on the potential anomaly. The updated scanning instructions may include scanning remaining voxels from the first scan at a second set of voxel sizes. Alternatively, the updated scanning instructions may include rescanning a previously scanned region at a second set of voxel sizes to improve the visibility or the detectable detail. Moreover, the updated scan plan and/or scanning instructions may include one or more different types of nuclei (e.g., having different Larmor frequencies), a different type of RF pulse sequence, a different MR technique (such as MRI, MR angiography or MRS to determine more information about the potential anomaly.

We now discuss determination of a scan plan and the scanning instructions in more detail. As noted previously, the system may determine a scan plan for the individual based on: age, gender, family history, a personal medical history, previous MR scans, previously detected anomalies, previous medical lab test results (such as blood tests, stool/biome tests, biopsies and other tissue samples, urine tests, etc.), previous medical imaging results (x-rays, CT scans, ultrasound, etc.), previous scanning instructions (such as a recommended scan time), doctor's instructions (such as an instruction to scan the kidney), requests from the individual (such as a report of knee pain), information in the biovault for one or more other individuals (such as individuals with similar medical contexts, pathologies or risks) and/or, more generally, information that specifies one or more risk factors for different pathologies. In order to determine the scan plan, the system may first determine risk factors or scores based on information in the biovault.

In some embodiments, the system may gather information associated with or specifying the risk factors for the individual. For example, the individual, a researcher, a medical doctor, a technician, a nurse, or another healthcare professional may enter information specifying the risk factors. Alternatively or additionally, the information associated with or specifying the risk factors can be accessed from an electronic medical record of the individual, downloaded from a social-media profile of the individual and/or may be collected from the individual using a wearable electronic device (such as a smartwatch, a smartphone, a personal fitness device, etc.). In particular, the information collected using the wearable electronic device may include: a vital sign (such as heartbeat data), pedometer data, sleep data, etc.

The scan plan may be computed by the system using a supervised-learning technique that is derived from or trained using the individual risk factors, historical MR scan data, radiologist diagnoses/classifications and/or, more generally, information included in the biovault. The supervised-learning technique may specify areas of interest within an individual's body and/or values in a look-up table that are used during analysis of MR signals from an MR scan. Note that the supervised-learning technique may include: a support vector machine, classification and regression trees, logistic regression, linear regression, nonlinear regression, a neural network, pattern recognition, a Bayesian technique, etc.

In some embodiments, when the individual arrives for a medical appointment or an MR scan appointment, the individual may access their medical information securely, as well as securely store the results of their MR scan(s) both before and after the MR scan(s). For example, an individual may use: a retinal scanner, a fingerprint scanner, an RFID token, a barcode, a login/passphrase and/or two-factor authentication scheme, or any other suitable authentication and authorization token or technique. The authentication and authorization information may allow the individual to unlock their medical data and/or to input risk-factor information to facilitate determination of the scan plan(s). Then, the system may access the necessary information of the individual, but may not need to have access to their name, address, phone number or other explicit personal identifying information. The MR scan plan can then proceed to scan areas of interest (e.g., predicted areas of concern where there may be potential anomalies), and can store the information securely using an encryption technique, such as a secure hash, a symmetric or an asymmetric encryption technique, etc.

When determining the scan plan, the system may use the individual's risk profile and MR scan history (if the individual has been scanned before). For example, if the individual has an MR scan history, previously detected anomalies or medical problems encountered since the last MR scan can be used to determine the scan plan. Based on the scan plan, the scanning instructions may specify one or more types of nuclei. Moreover, the scanning instructions may indicate that the MR scanner should perform a scan of the one or more types of nuclei at a first set of voxel sizes. The scanning instructions may include or may specify: magnetic gradients, the MR frequencies of RF pulses associated with a specific voxel size, a specific MR frequency associated with a specific type of nuclei, a specific MR frequency associated with a specific molecule, a specific tissue type, etc.

For example, the risk factor or score for localized skin cancer may be increased for a 42-year-old male with no personal medical history of skin cancer, but a family medical history of skin cancer, who has two large moles. In addition, an anomaly may have been detected in their knee in a previous MR scan. Consequently, the location on their knee may be added to the scan plan, and the scan plan may specify that the MR scan measure $^{19}$F Fluoride and a smaller voxel size when detecting $^1$H nuclei. In this way, the MR scan of the knee can be captured in greater detail for a radiologist or another healthcare professional to review.

The system may compute the voxel size or a set of voxel sizes in the scanning instructions based on the scan plan. Moreover, the system may determine the organ(s) or tissue to be scanned, the location(s) in the body, and the type of nuclei to be detected. In general, the voxel size may depend on the organ, the location in the body and the type of nuclei.

Thus, if the anomaly in the knee was previously detected using a 1 mm$^3$ isometric voxel size, a small voxel size may be selected. For example, the voxel size in the current MR scan may be a 0.1 mm$^3$ isometric voxel to capture the anomaly in more detail and to provide the best possible balance between identification in the MR signals and the MR signals capture time.

As discussed previously, the voxel size may be chosen based on the type of nuclei that is to be detected. The MR signal that is measured is primarily limited by the gyromagnetic ratio of the type of nuclei as well as the concentration of the type of nuclei in the volume defined by a voxel. Note that it may not always practical to choose the smallest possible voxel size because increasing the density of voxels per unit volume can require more encoding operations, which in turn can result in longer acquisition or scan times. Therefore, in order to optimize scan times, MR scanner utilization, and the accuracy of anomaly detection, the system may pre-define or pre-select a first order set that includes a 'summary' voxel size, MR spectra and pulse sequence(s) that may be specific to organs or regions in the body. This first order set can enable an initial or first scan to collect enough information so that potential anomalies can be at least statistically detected. In addition, more-detailed information can be collected in real time (i.e., during an MR scan) when a potential anomaly is detected.

In general, a number of different factors can be used to compute the initial summary voxel sizes. This same information can also be used to determine how to tune the voxel sizes and MR spectral sensitivities in order to collect more detailed information when a potential anomaly is detected. We now describe several of these factors in more detail, including: the gyromagnetic ratio, $T_1$ and $T_2$ relaxation times, estimated abundance, volumetric size of organs or body structures, medical risk factors and correlations and/or previous MR scan data.

The gyromagnetic ratio of a type of nuclei can be used to estimate the MR signal the system expects to see for a specific voxel size and MR spectrum within a healthy or a diseased organ, or another structure in the individual. As described previously, a variety of metabolites or properties can be detected using different types of nuclei.

Moreover, as summarized in Table 1, different tissues can be characterized by different $T_1$ and $T_2$ relaxation times.

TABLE 1

| Tissue | $T_1$ (s) | $T_2$ (ms) |
|---|---|---|
| Cerebrospinal Fluid | 0.8-20 | 110-2000 |
| White Matter | 0.76-1.08 | 61-100 |
| Gray Matter | 1.09-2.15 | 61-109 |
| Meninges | 0.5-2.2 | 50-165 |
| Muscle | 0.95-1.82 | 20-67 |
| Adipose | 0.2-0.75 | 53-94 |

Furthermore, different types of nuclei and chemicals are known to have different nominal concentrations or abundance in different organs and structures within the body. Certain pathologies of different organs and structures of the body also have unique chemical signatures that may contain higher or lower concentrations with respect to other regions of the body. Knowledge of this information a priori can be used to aid in determining optimal voxel sizes and spectral sensitivities for specific organs and regions of the body based on the purpose of the MR scan, e.g., as indicated in the scan plan. As more data is collected, both on an individual basis and across the general population in the biovault, the nominal and pathological chemical signatures and concentrations for different organs can be refined and segmented to further customize and tune the optimal scan plan for each individual.

The volume of structures and organs in an individual can also be used to computer voxel sizes in order to optimize acquisition or scan times. For example, it may take longer to scan the same voxel size in a bigger heart than a smaller heart, so an adjustment to the voxel size may be proportional to the volumetric size of organs or body structures. In particular, instead of using a 1 mm$^3$ isometric voxel for a median-sized male heart, if the heart volume for a male is estimated to be 20% larger than the median heart, then an isometric voxel size of 1.0626 mm on a side can be used (note that $1.2^{1/3}$ equals 1.0626) to ensure that the MR scan has a similar scan time.

Furthermore, medical risk factors and correlations may include, but are not limited to, age, gender, blood work, urine samples, stool samples, personal or family medical histories, which may suggest that certain organs or structures in an individual's body should be scanned at specific voxel sizes in certain MR spectra in order to increase the likelihood of detecting anomalies associated with pathologies for which the individual is potentially at risk. For example, sodium spectra tend to show up in cartilage, so when evaluating the knees of an individual that is over age forty, sodium spectra imaging may be selected to evaluate their knee cartilage.

Additionally, data from previous MR scans of an individual having anomalies or regions of interest that need to be monitored over time may also aid in determining the optimal voxel size and MR spectral sensitivities in the scan plan and/or the scanning instructions for this individual.

In some embodiments, prior to performing an MR scan, a series of pre-scan operations may be performed. For example, if the MR scan is the first MR scan, a more comprehensive questionnaire and checklist for family history may be included, and permission may be obtained to retrieve existing medical records and store them in the biovault with other medical information for the individual. In addition, a cancer screen may be performed to determine if the individual has a genetic pre-disposition to specific types of cancer that should be monitored. Alternatively, if the MR scan is not the first MR scan, then the previously collected information and previous MR scans can be used as a guide.

Moreover, the individual's height, weight, blood pressure, blood oxygen levels, impedance or hydration level may be measured. Furthermore, sugar water may be administered to improve contrast in MM. Then, high-resolution pictures may be captured of the individual's eyes, nose, throat, ears, and/or skin, as well as a thermal image of their body. The individual may also provide a urine sample, a blood sample, a saliva sample and/or a stool sample, which may be used to assess hydration, and to perform basic assays, a full blood panel, microbiome analysis, genetic sequencing or next generation sequencing and/or refractometry (i.e., to measure the index of refraction). Additionally, the individual may be asked a series of questions to assess any recent changes in their health or symptoms they may be experiencing.

Next, this information, as well as other information in the biovault, may be used to determine the scan plan and the scanning instructions. Based on the scanning instructions, the MR scanner may perform a whole-body MR scan. This MR scan may include: high-resolution full-body morphology (which may accurately locate organs and bones in 3D space that can be used as a map in the remainder of the MR scan or during segmentation of MR images); whole-body GluCEST with sugar-water contrast; full-body MR angiography and blood-velocity flow imaging; full-body diffusion-weighted imaging; full-body susceptibility-weighted imaging; full-body MRT; MRI of specific body parts, including the head, chest, heart (with sodium imaging in parallel, which can be captured using a dual-tuned surface coil), abdomen (including the liver, kidney, stomach, pancreas, prostate, colon, etc.); and MRE on the previously disclosed tissues.

We now describe the biovault and its use in more detail. In general, tissue samples from most non-diseased individuals in hospitals are evaluated by a medical specialist (such as a pathologist) and then destroyed. However, government regulations and laws often require that certain pathology samples are stored for a specific amount of time before they can be destroyed. Currently, there are no large standardized and quantitative datasets that contain information for symptomatic and asymptomatic individuals for comparison and improvement of medical diagnoses and that allow researchers to compare new individuals against an archive of historical measurements.

In order to address this need, the indexed MR signals and/or the associated invariant MR signatures may be characterized and normalized quantitatively so that their digital representation can be uploaded to a service where analysis techniques can, in real-time or near real-time, compare the sample quantitatively to a vast data structure (such as the biovault, which is sometimes referred to as a 'pathology characteristics knowledge base' or a 'pathology knowledge base') containing numerous previously measured and indexed ex vivo samples, in vivo samples and/or information about individuals (including those for fresh or 'wet' tissue samples, frozen samples, formalin fixed-paraffin embedded tissue samples, information from MR scans, etc.). This capability may require that the measurement technique be largely invariant to the type of sample being indexed, the MR scanner used, as well as the pulse sequences and the magnitude of the magnetic fields (or the magnetic-field strengths) used to index the tissue samples or the information about the individuals. For example, the data structure may include invariant MR signatures that can be used to generate MR fingerprints for arbitrary scanning conditions (such as an arbitrary magnetic field $B_0$ and an arbitrary pulse sequence), and the generated MR fingerprints may be compared to a measured MR fingerprint.

Note that the biovault may include a set of statistical definitions of pathology based on research, clinical definitions, as well as correlations have previous pathological cases used to compute per pathology risk scores. The pathology risk scores can be computed for a specific individual for a specific pathology that includes but is not limited to the statistical probability that the individual has a specific pathology or is at risk to develop a specific pathology in the future. The pathology risk scores can be stored in a look-up table based on the invariant MR signatures. Alternatively, the pathology risk scores may be stored in a look-up table based on MR signals, MR spectra and/or MR fingerprints, which each may be representations or projections of the invariant MR signatures in particular contexts, such as for a particular MR scanner having particular characteristics and particular scanning instructions. Furthermore, the invariant MR signatures may be linked to specific pathologies and diseases, as determined from scans of 'known good' and 'known bad' individuals or tissue samples, negative and positive-result biopsies, higher-specificity scans performed around particular or anomalous regions, radiologist feedback, etc. The biovault can be manually updated by technicians, researchers, doctors, journals, or other sources. Alternatively or additionally, the biovault may be automatically updated with additional tissue-sample or MR-scan information, and/or using a crawler that analyzes scientific publications and automatically extracts or scrapes research results and translates them or integrates them into pathology risk scores.

In some embodiments, the biovault includes one or more dimensional animations of a body or a portion of a body over time (e.g., over weeks, months or years, or during a surgery) based on multiple invariant MR signatures of an individual that are acquired at different times.

The creation of this data structure may aid in the detection of pathological tissue in vivo or even during scans by allowing the differences between healthy and unhealthy tissue to be classified or to identify other anomalous tissue that has not been previously classified with reduced false-positive rates. (In particular, the biovault may provide more accurate pathological risk scores because of its size, with millions or billions of data points, and the ongoing integrated radiologist feedback, which facilitates continuous learning/improvement.) This capability may help determine the portions or regions of an individual that may require more detailed scans of detected anomalies. For example, an analysis technique (such as a supervised-learning technique, e.g., a support vector machine, classification and regression trees, logistic regression, linear regression, nonlinear regression, a neural network, a Bayesian technique, etc.) may classify detected anomalies as healthy or unhealthy tissue based on previous measurements and classifications in the data structure and features in MR signals measured in a current scan. Alternatively or additionally, images may be provided to radiologists or pathologists who specialize in the type of tissue or the anomaly detected, and the radiologists or pathologists may confirm the analysis or may classify the individual.

In this way, MR signals acquired for tissue in individuals, whether benign or non-benign, can be indexed, and known-healthy (e.g., whitelisted tissue) and known-anomalous tissue (e.g., blacklisted tissue) can be determined, and unknown tissue in a grey zone (e.g., greylisted tissue) can be classified. The unknown tissue may be marked for inspection using other MR techniques, additional related biopsies, radiologist or pathologist review, and/or using another analysis technique.

Note that the invariant MR signatures may be used to improve detection of anomalies on an individual basis. In particular, what is normal in one individual may be slightly different than what is normal in another individual, and clusters of individuals reflecting various shades or gradations of 'normal' can help classify tissue. (Thus, in some embodiments, the measurement technique may include an unsupervised-learning technique, such as clustering, to group or classify similar individuals to facilitate classification.) Stated differently, the biovault may allow the information and data for different individuals to be interpreted in their medical context (such as a person's past injuries, activities, and environment), thereby increasing the accuracy of pathological risk scores that are computed for these individuals. As noted previously, the amount of data that can be captured about each individual may be much larger than the amount of data that can be processed by a single pathologist or radiologist or even a team of radiologists and pathologists. The invariant MR signatures in the biovault may be used to compensate for or eliminate this limitation or constraint.

As more individuals are scanned and indexed, the biovault will include an ever larger knowledge base of tissue characteristics and structures in the body. This will allow the system to model individuals' bodies, at the voxel level, in multiple dimensions (including tissue and chemical characteristics) as a function of time. In addition, the system will be able to combine the models for different individuals into meta-models (i.e., aggregated models for multiple individuals) that are segmented based on age, gender and other factors in the biovault to accurately determine anomalies and pathological risk scores. For example, when indexing a specific region of an individual's brain, if a chemical signature exists in a concentration more than 3 standard deviations outside the average concentration against a million individuals of the same age and gender it may indicate an anomaly. More sophisticated models may be used to define an anomaly, and these models may be organ or region specific in the body and/or for a subset of the population. Thus, over time, the system may be able to automatically cluster individuals into subpopulations that accurately predict the risk of different pathologies. In particular, given a large enough body of data, the system may be able to determine an individual's risk for developing arthritis in their knee by correlating cartilage degeneration with people that may have larger than average differences in the length of their femur or tibia. Such correlations have typically not been determined previously on a large scale because the data did not exist to do so. Therefore, the biovault may open up a new era in understanding of the human body and may result in a number of health applications that will improve the quality of life for many people.

In some embodiments, the invariant MR signature from a previous MR scan of an individual (or a related or similar individual) is used as a target for comparison to the MR signals during a current scan of the individual. For example, the previous invariant MR signature may be used to generate estimated or simulated MR signals for voxels in an individual in the current scan based on the characteristics of an MR scanner and/or the scanning instructions. In particular, the previous invariant MR signature may include or may specify parameters in an MR model that can be used, in conjunction with the characteristics of an MR scanner and/or the scanning instructions, to generate the estimated MR signals. Subsequently, the estimated MR signals can be used as a target to compare with the MR signals in the current scan. This may allow rapid identification of areas or regions with unexpected changes, which may allow identification of the parts or regions of the individual that may require more detailed scans of detected anomalies and/or measurement of different parameters (i.e., which may allow a scan plan to be dynamically updated). This capability may allow more efficient (i.e., faster) and more accurate scans of the individual, such as by allowing: different scanning instructions, different MR techniques, and/or different voxels sizes to be used in different portions or regions of the individual (e.g., larger voxels sizes in less interesting regions and smaller voxel sizes in regions that require more detailed scans).

Thus, the measurement technique may allow hospitals and research institutions to catalogue and index many or even all of the MR signals associated with different individuals in a searchable way, and may allow a large data structure of indexed symptomatic and asymptomatic individuals to be amassed and used in an efficient manner (i.e., the measurement technique may be scaled to a large number of individuals) to provide clinically relevant results.

For example, when a region of interest is identified in an individual (manually by an operator or technician and/or automatically based on comparisons with simulated or estimated MR signals based on previous invariant MR signatures for this individual), a search may be automatically performed against the stored invariant MR signatures for other individuals and/or clinical research that have similar region(s) based on tissue parameters in the region of interest. These searches may surface similar cases and outcomes, with known diagnoses, to a radiologist analyzing the measurements on the individual.

While the preceding discussion illustrated the use of MR techniques in the measurement technique, this approach may be generalized to a measurement system that is able to physically model and measure a material in real-time using a wide variety of measurement techniques (including one or more of the other measurements performed on the individual). In general, this measurement system can use a combination of mechanical and/or electromagnetic waves to 'perturb' the volume being scanned in order to evaluate the correctness of a prediction in terms of how the volume will respond to these perturbations. This also includes the ability for the measurement system to simulate itself and any part of the environment in which the measurement system is located that could affect the correctness of the predictive model the measurement system is trying to generate to describe the volume being scanned.

Note that the different measurement techniques may provide tensor-field mapping and the ability to detect anomalies in tensor fields. These maps can be images or quantitative tensor field maps, and each of the measurements technique may provide a visualization of a different type of tensor field map captured with a different measurement technique. By looking at or considering two or more of these maps, of the measurement system may have access to orthogonal information.

Thus, the measurement system may provide a way to capture, in real-time or near real-time, higher-order or hyper-dimensional pseudo-tensors or matrices at each voxel in 3D space. Using electromagnetic and/or mechanical perturbations, the measurement system may use different measurement techniques to measure disturbances and responses, and then to simulate the responses. Moreover, the measurement system may iterate this process based on differences between the measured and the simulated responses. For example, during the iteration, the sampling frequency, the measurement technique, etc. may be modified to determine additional information that is subsequently used to refine the simulations and to reduce the differences. Stated differently, the next perturbation or disturbance may be chosen to minimize the error of the difference across the hyper-dimensional space. Note that this adaptation or learning may be based on one or more supervised learning techniques (such as a deep-learning technique) and/or a non-deterministic approach (such as a heuristic).

Consequently, the hyper-dimensional matrices at the voxels may not have a fixed resolution and/or a fixed set of captured parameters. Instead, this information (such as a sparsity of the matrices) may vary based on the results of previous scans and/or a current scan. For example, coarse scans may be followed by fine-resolutions scans of particular regions or features that are of interest based on constraints, such as a prior knowledge (e.g., a medical history of one or more individuals, etc.).

The result of this characterization may be a (4+N)D (three spatial dimensions, one time dimension, and N measurement dimensions at each point in space) quantitative model of the volume being scanned. Thus, the measurement technique may involve MR techniques other than MRI or may include MRI. Note that the (4+N)D quantitative model may be projected onto an arbitrary subset of the full (4+N)D space, including 2D or 3D images.

In some embodiments, the use of multidimensional data and models provides enhanced diagnostic accuracy (i.e., a lower false-positive rate) relative to conventional MRI approaches, even if a larger voxel size is used. Thus, the measurement technique may allow improved diagnostic accuracy with a larger voxel size than would be needed in conventional MRI.

Note that the multi-dimensional data (such as the MR models) in the biovault may be used for a variety of purposes. For example, a 3D model of an individual may be used as a reference about the structure of the individual's body, such that, if the individual suffers a fracture or a broken bone, the 3D model may be used to guide 3D printing or customization of a cast or a replacement part or insert. Because such a cast or insert may fit the individual's anatomy quite well, it may provide faster and improved healing and, thus, improved long-term mobility.

Figure 8:
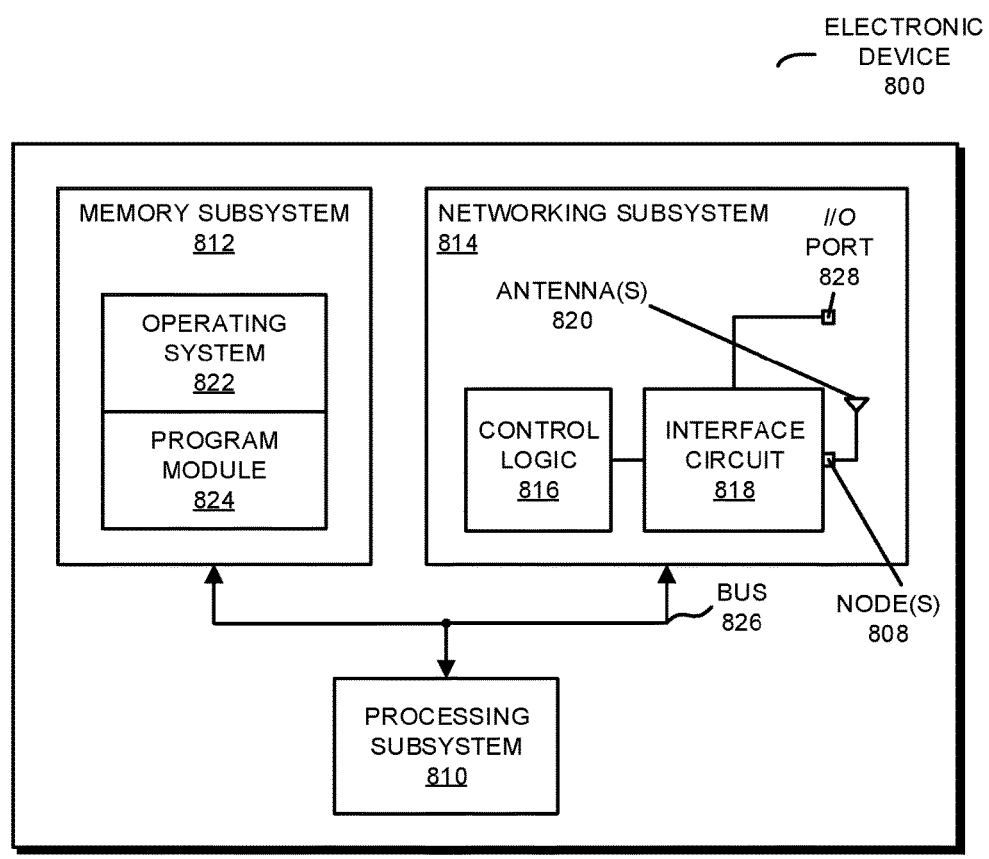
FIG. 8 is a block diagram illustrating an electronic device in the system of FIG. 1 in accordance with an embodiment of the present disclosure.

We now further describe an electronic device that performs at least some of the operations in measurement technique. FIG. 8 presents a block diagram illustrating an example of an electronic device 800 in system 100 (FIG. 1), such as computer system 114 (FIG. 1) or another of the computer-controlled components in system 100 (FIG. 1). This electronic device includes a processing subsystem 810, memory subsystem 812, and networking subsystem 814. Processing subsystem 810 may include one or more devices configured to perform computational operations and to control components in system 100 (FIG. 1). For example, processing subsystem 810 may include one or more microprocessors, one or more graphics processing units (GPUs), application-specific integrated circuits (ASICs), microcontrollers, programmable-logic devices, and/or one or more digital signal processors (DSPs).

Memory subsystem 812 may include one or more devices for storing data and/or instructions for processing subsystem 810 and networking subsystem 814. For example, memory subsystem 812 may include dynamic random access memory (DRAM), static random access memory (SRAM), and/or other types of memory. In some embodiments, instructions for processing subsystem 810 in memory subsystem 812 include one or more program modules 824 or sets of instructions, which may be executed in an operating environment (such as operating system 822) by processing subsystem 810. Note that the one or more computer programs may constitute a computer-program mechanism or a program module (i.e., software). Moreover, instructions in the various modules in memory subsystem 812 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 810.

In addition, memory subsystem 812 may include mechanisms for controlling access to the memory. In some embodiments, memory subsystem 812 includes a memory hierarchy that comprises one or more caches coupled to a memory in electronic device 800. In some of these embodiments, one or more of the caches is located in processing subsystem 810.

In some embodiments, memory subsystem 812 is coupled to one or more high-capacity mass-storage devices (not shown). For example, memory subsystem 812 may be coupled to a magnetic or optical drive, a solid-state drive, or another type of mass-storage device. In these embodiments, memory subsystem 812 may be used by electronic device 800 as fast-access storage for often-used data, while the mass-storage device is used to store less frequently used data.

In some embodiments, memory subsystem 812 includes a remotely located archive device. This archive device can be a high-capacity network attached mass-storage device, such as: network attached storage (NAS), an external hard drive, a storage server, a cluster of servers, a cloud-storage provider, a cloud-computing provider, a magnetic-tape backup system, a medical records archive service, and/or another type of archive device. Moreover, processing subsystem 810 may interact with the archive device via an application programming interface to store and/or access information from the archive device. Note that memory subsystem 812 and/or electronic device 800 may be compliant with the Health Insurance Portability and Accountability Act.

Figure 9:
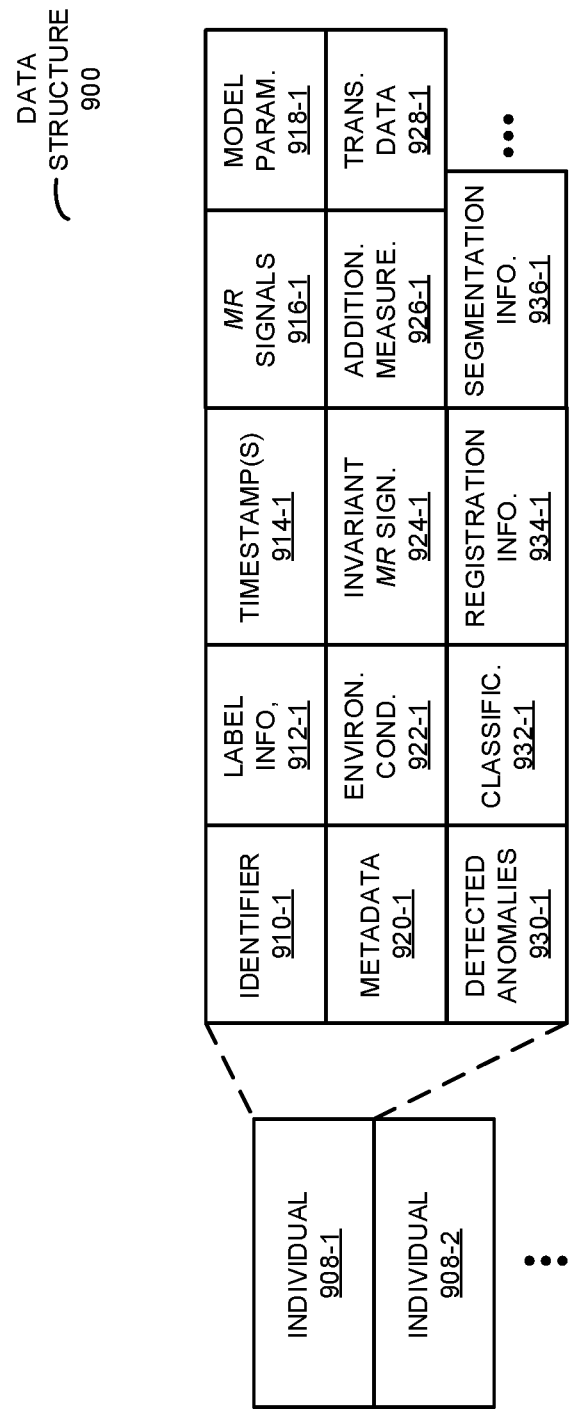
FIG. 9 is a drawing illustrating a data structure that is used by the electronic device of FIG. 8 in accordance with an embodiment of the present disclosure.

An example of the data stored (locally and/or remotely) in memory subsystem 812 is shown in FIG. 9, which presents a drawing illustrating an example of a data structure 900 that is used by electronic device 800 (FIG. 8). This data structure may include: an identifier 910-1 of individual 908-1, label information 912 (such as age, gender, biopsy results and diagnosis if one has already been made and/or any other suitable sample information), timestamps 914 when data was acquired, received MR signals 916 (and, more generally, raw data), MR capture and model parameters 918 (including the voxel size, speed, resonant frequency, $T_1$ and $T_2$ relaxation times, signal processing techniques, RF pulse techniques, magnetic gradient strengths, the variable magnetic field $B_0$, the pulse sequence, etc.), metadata 920 (such as information characterizing individual 908-1, demographic information, family history, optional segmentation data, data generated from or in response to the raw data, etc.), environmental conditions 922 (such as the temperature, humidity and/or barometric pressure in the room or the chamber in which individual 908-1 was measured), a determined invariant MR signature 924, one or more additional measurements 926 of physical properties of individual 908-1 (such as weight, dimensions, images, etc.), transformed data 928 generated from or in response to MR signals 916 (such as an estimated invariant MR signature), optional detected anomalies 930 (which, for a particular voxel, may include information specifying one or more of detected anomalies 930), optional classifications 932 of detected anomalies 930), registration information 934 and/or segmentation information 936. Note that data structure 900 may include multiple entries for different scanning instructions.

In one embodiment, data in data structure 900 is encrypted using a block-chain or a similar cryptographic hash technique to detect unauthorized modification or corruption of records. Moreover, the data can be anonymized prior to storage so that the identity of an individual is anonymous unless the individual gives permission or authorization to access or release the individual's identity.

Referring back to FIG. 8, networking subsystem 814 may include one or more devices configured to couple to and communicate on a wired, optical and/or wireless network (i.e., to perform network operations and, more generally, communication), including: control logic 816, an interface circuit 818, one or more antennas 820 and/or input/output (I/O) port 828. (While FIG. 8 includes one or more antennas 820, in some embodiments electronic device 800 includes one or more nodes 808, e.g., a pad or connector, which can be coupled to one or more antennas 820. Thus, electronic device 800 may or may not include one or more antennas 820.) For example, networking subsystem 814 can include a Bluetooth networking system (which can include Bluetooth Low Energy, BLE or Bluetooth LE), a cellular networking system (e.g., a 3G/4G network such as UMTS, LTE, etc.), a universal serial bus (USB) networking system, a networking system based on the standards described in IEEE 802.11 (e.g., a Wi-Fi networking system), an Ethernet networking system, and/or another networking system.

Moreover, networking subsystem 814 may include processors, controllers, radios/antennas, sockets/plugs, and/or other devices used for coupling to, communicating on, and handling data and events for each supported networking system. Note that mechanisms used for coupling to, communicating on, and handling data and events on the network for each network system are sometimes collectively referred to as a 'network interface' for network subsystem 814. Moreover, in some embodiments a 'network' between components in system 100 (FIG. 1) does not yet exist. Therefore, electronic device 800 may use the mechanisms in networking subsystem 814 for performing simple wireless communication between the components, e.g., transmitting advertising or beacon frames and/or scanning for advertising frames transmitted by other components.

Within electronic device 800, processing subsystem 810, memory subsystem 812, networking subsystem 814 may be coupled using one or more interconnects, such as bus 826. These interconnects may include an electrical, optical, and/ or electro-optical connection that the subsystems can use to communicate commands and data among one another. Although only one bus 826 is shown for clarity, different embodiments can include a different number or configuration of electrical, optical, and/or electro-optical connections among the subsystems.

Electronic device 800 may be (or can be) included in a wide variety of electronic devices. For example, electronic device 800 may be included in: a tablet computer, a smartphone, a smartwatch, a portable computing device, test equipment, a digital signal processor, a cluster of computing devices, a laptop computer, a desktop computer, a server, a subnotebook/netbook and/or another computing device.

Although specific components are used to describe electronic device 800, in alternative embodiments, different components and/or subsystems may be present in electronic device 800. For example, electronic device 800 may include one or more additional processing subsystems, memory subsystems, and/or networking subsystems. Additionally, one or more of the subsystems may not be present in electronic device 800. Moreover, in some embodiments, electronic device 800 may include one or more additional subsystems that are not shown in FIG. 8.

Although separate subsystems are shown in FIG. 8, in some embodiments, some or all of a given subsystem or component can be integrated into one or more of the other subsystems or components in electronic device 800. For example, in some embodiments the one or more program modules 824 are included in operating system 822. In some embodiments, a component in a given subsystem is included in a different subsystem. Furthermore, in some embodiments electronic device 800 is located at a single geographic location or is distributed over multiple different geographic locations.

Moreover, the circuits and components in electronic device 800 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 814 (such as a radio) and, more generally, some or all of the functionality of electronic device 800. Moreover, the integrated circuit may include hardware and/or software mechanisms that are used for transmitting wireless signals from electronic device 800 and receiving signals at electronic device 800 from other components in system 100 (FIG. 1) and/or from electronic devices outside of system 100 (FIG. 1). Aside from the mechanisms herein described, radios are generally known in the art and hence are not described in detail. In general, networking subsystem 814 and/or the integrated circuit can include any number of radios. Note that the radios in multiple-radio embodiments function in a similar way to the radios described in single-radio embodiments.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

In addition, in some of the preceding embodiments there are fewer components, more components, a position of a component is changed and/or two or more components are combined.

In the preceding description, we refer to 'some embodiments.' Note that 'some embodiments' describes a subset of all of the possible embodiments, but does not always specify the same subset of embodiments.

While the preceding discussion used one or more MR techniques as an illustrative example, in other embodiments the measurement technique is used in conjunction with one or more alternative or additional non-invasive imaging or measurement techniques, such as: computed tomography, ultrasound, x-ray, positron emission spectroscopy, electron spin resonance, optical/infrared spectroscopy (e.g., to determine a complex index of refraction at one or more wavelengths), electrical impedance at DC and/or an AC frequency, proton beam, photoacoustic, etc. In particular, using one or more of these alternative or additional non-invasive imaging or measurement techniques, quantitative comparisons of non-invasive imaging or measurements and simulated or computed measurements may be used to iteratively update measurement instructions and/or to detect potential anomalies.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A system to perform a magnetic-resonance (MR) scan, comprising:
    an MR scanner that is configured to perform one or more MR scans of at least a first portion of a biological lifeform;
    an interface circuit electrically coupled to the MR scanner, wherein the interface circuit is configured to communicate information with the MR scanner, and
    wherein the system is configured to:
        provide, to the MR scanner, first scanning instructions based on an initial scan plan to capture first MR signals of one or more first types of nuclei in at least the first portion of the biological lifeform, wherein the first MR signals are associated with first voxels having first sizes at first three-dimensional (3D) positions in at least the first portion of the biological lifeform;
        perform, based on the first scanning instructions, a first MR scan of the biological lifeform using the MR scanner;
        receive, from the MR scanner, the first MR signals;
        analyze the first MR signals to detect a potential anomaly in the first MR signals based on a first template of a potential anomaly and one or more of: a medical history of the biological lifeform; and an MR-scan history of the biological lifeform that includes prior MR scans of the biological lifeform, wherein the first template of the potential anomaly includes simulated MR signals, associated with the MR scanner, of the one or more first types of nuclei at the first voxels in at least the biological lifeform, and wherein generating the simulated MR signals involves calculating the simulated MR signals in a forward calculation using a previously determined invariant MR signature, predetermined characteristics of the MR scanner, simulation of noise, and the first scanning instructions, and wherein the previously determined invariant MR signature describes dynamic MR responses of voxels at 3D positions in the biological lifeform at arbitrary magnetic-field strength and is independent of a second MR scanner and a set of scanning instructions used to acquire a set of MR signals at different magnetic-field strengths that, via an inverse calculation, specify the invariant MR signature;
        when the potential anomaly is detected, dynamically modify the initial scan plan based on the detected potential anomaly and one or more of the medical history and the MR-scan history, wherein the modified scan plan includes one or more second types of nuclei in second voxels, having associated second sizes, in at least a second portion of the biological lifeform, and wherein the second sizes are smaller than the first sizes;
        interrupt the initial scan plan;
        provide, to the MR scanner, second scanning instructions based on the modified scan plan to capture second MR signals of the one or more second types of nuclei in at least the second portion of the biological lifeform, wherein the second MR signals are associated with the second voxels at second 3D positions in at least the second portion of the biological lifeform;
        perform, based on the second scanning instructions, a second MR scan of the biological lifeform using the MR scanner; and
        receive, from the MR scanner, the second MR signals.

2. The system of claim 1, wherein the system is further configured to generate the initial scan plan for at least the first portion of the biological lifeform based on the medical history and the MR-scan history; and
wherein the initial scan plan includes the one or more first types of nuclei in the first voxels, having the first sizes, in at least the first portion of the biological lifeform.

3. The system of claim 1, wherein the system is further configured to classify each of the voxels associated with the detected potential anomaly as having one of: a risk of misclassification that is less than a threshold value; the risk misclassification that is greater than the threshold value; and the risk misclassification that is unknown.

4. The system of claim 1, wherein at least the second portion of the biological lifeform corresponds to the 3D positions of the detected potential anomaly.

5. The system of claim 4, wherein the second voxel sizes and at least the second portion of the biological lifeform are computed from a size of the detected potential anomaly.

6. The system of claim 1, wherein the system is further configured to analyze the second MR signals to improve an accuracy of the detected potential anomaly based on one or more of: the medical history; the MR-scan history; and a second template of the potential anomaly.

7. The system of claim 6, wherein the second template of the potential anomaly includes simulated MR signals of the one or more second types of nuclei at the second voxels in at least the biological lifeform.

8. The system of claim 1, wherein the first MR signals include a first MR image and the second MR signals include a second MR image.

9. The system of claim 1, wherein the second scanning instructions correspond to one of: magnetic-resonance spectroscopy (MRS), magnetic-resonance thermometry (MRT), magnetic-resonance elastography (MRE), MR fingerprinting, and diffusion-tensor imaging.

10. The system of claim 1, wherein the system is further configured to analyze adjacent voxels associated with the detected potential anomaly to determine a metabolic chemical signature in magnetic-resonance spectroscopy (MRS).

11. The system of claim 1, wherein analyzing the first MR signals involves aligning the first MR signals in the first voxels with anatomical landmarks of the biological lifeform in a prior MR scan of the biological lifeform and comparing the aligned first MR signals in the first voxels to prior first MR signals in the first voxels in the prior MR scan.

12. The system of claim 1, wherein the second voxel sizes and at least the second portion of the biological lifeform are based on a location in the biological lifeform of the potential anomaly.

13. The system of claim 1, wherein the system is further configured to:
provide, to the MR scanner, third scanning instructions based on the initial scan plan to capture third MR signals of the one or more first types of nuclei in a third portion of the biological lifeform, wherein the third MR signals are associated with the first voxels at third 3D positions in at least the third portion of the biological lifeform; and
receive, from the MR scanner, the third MR signals, wherein the third MR signals complete the initial scan plan from a position where it was stopped.

14. The system of claim 1, wherein the system is further configured to determine a recommended time for a subsequent MR scan of the biological lifeform based on one or more of: the medical history; the MR-scan history; and the detected potential anomaly.

15. The system of claim 1, wherein the initial scan plan is dynamically modified based on detection of another potential anomaly in a second biological lifeform.

16. A non-transitory computer-readable storage medium for use in conjunction with a system that includes a magnetic-resonance (MR) scanner, the computer-readable storage medium storing a program module that, when executed by the system, causes the MR scanner to perform an MR scan by performing at least the operations comprising:
providing, to the MR scanner, first scanning instructions based on an initial scan plan to capture first MR signals of one or more first types of nuclei in at least the first portion of the biological lifeform, wherein the first MR signals are associated with first voxels having first sizes at first three-dimensional (3D) positions in at least the first portion of the biological lifeform;
performing, based on the first scanning instructions, a first MR scan of the biological lifeform using the MR scanner;
receiving, from the MR scanner, the first MR signals;
analyzing the first MR signals to detect a potential anomaly in the first MR signals based on a first template of a potential anomaly and one or more of: a medical history of the biological lifeform; and an MR-scan history of the biological lifeform that includes prior MR scans of the biological lifeform, wherein the first template of the potential anomaly includes simulated MR signals, associated with the MR scanner, of the one or more first types of nuclei at the first voxels in at least the biological lifeform, wherein generating the simulated MR signals involves calculating the simulated MR signals in a forward calculation using a previously determined invariant MR signature, predetermined characteristics of the MR scanner, simulation of noise, and the first scanning instructions, and wherein the previously determined invariant MR signature describes dynamic MR responses of voxels at 3D positions in the biological lifeform at arbitrary magnetic-field strength and is independent of a second MR scanner and a set of scanning instructions used to acquire a set of MR signals at different magnetic-field strengths that, via an inverse calculation, specify the invariant MR signature;
when the potential anomaly is detected, dynamically modifying the initial scan plan based on the detected potential anomaly and one or more of the medical history and the MR-scan history, wherein the modified scan plan includes one or more second types of nuclei in second voxels, having associated second sizes, in at least a second portion of the biological lifeform, and wherein the second sizes are smaller than the first sizes;
interrupting the initial scan plan;
providing, to the MR scanner, second scanning instructions based on the modified scan plan to capture second MR signals of the one or more second types of nuclei in at least the second portion of the biological lifeform, wherein the second MR signals are associated with the second voxels at second 3D positions in at least the second portion of the biological lifeform;
performing, based on the second scanning instructions, a second MR scan of the biological lifeform using the MR scanner; and
receiving, from the MR scanner, the second MR signals.

17. A method for performing a magnetic-resonance (MR) scan using a system that includes an MR scanner, the method comprising:
by the system:
providing, to the MR scanner, first scanning instructions based on an initial scan plan to capture first MR signals of one or more first types of nuclei in at least the first portion of the biological lifeform, wherein the first MR signals are associated with first voxels having first sizes at first three-dimensional (3D) positions in at least the first portion of the biological lifeform;

performing, based on the first scanning instructions, a first MR scan of the biological lifeform using the MR scanner;

receiving, from the MR scanner, the first MR signals;

analyzing the first MR signals to detect a potential anomaly in the first MR signals based on a first template of a potential anomaly and one or more of: a medical history of the biological lifeform; and an MR-scan history of the biological lifeform that includes prior MR scans of the biological lifeform, wherein the first template of the potential anomaly includes simulated MR signals, associated with the MR scanner, of the one or more first types of nuclei at the first voxels in at least the biological lifeform, wherein generating the simulated MR signals involves calculating the simulated MR signals in a forward calculation using a previously determined invariant MR signature, predetermined characteristics of the MR scanner, simulation of noise, and the first scanning instructions, and wherein the previously determined invariant MR signature describes dynamic MR responses of voxels at 3D positions in the biological lifeform at arbitrary magnetic-field strength and is independent of a second MR scanner and a set of scanning instructions used to acquire a set of MR signals at different magnetic-field strengths that, via an inverse calculation, specify the invariant MR signature;

when the potential anomaly is detected, dynamically modifying the initial scan plan based on the detected potential anomaly and one or more of the medical history and the MR-scan history, wherein the modified scan plan includes one or more second types of nuclei in second voxels, having associated second sizes, in at least a second portion of the biological lifeform, and wherein the second sizes are smaller than the first sizes;

interrupting the initial scan plan;

providing, to the MR scanner, second scanning instructions based on the modified scan plan to capture second MR signals of the one or more second types of nuclei in at least the second portion of the biological lifeform, wherein the second MR signals are associated with the second voxels at second 3D positions in at least the second portion of the biological lifeform;

performing, based on the second scanning instructions, a second MR scan of the biological lifeform using the MR scanner; and receiving, from the MR scanner, the second MR signals.

18. The system of claim 1, wherein, when detected potential anomaly is associated with a presence of metal, the modified scan plan includes MR measurements of the potential anomaly using a safe magnetic-field strength.

19. The computer-readable storage medium of claim 16, wherein, when detected potential anomaly is associated with a presence of metal, the modified scan plan includes MR measurements of the potential anomaly using a safe magnetic-field strength.

20. The method of claim 17, wherein, when detected potential anomaly is associated with a presence of metal, the modified scan plan includes MR measurements of the potential anomaly using a safe magnetic-field strength.

21. The computer-readable storage medium of claim 16, wherein the one or more operations comprise analyzing the second MR signals to improve an accuracy of the detected potential anomaly based on one or more of: the medical history; the MR-scan history; and a second template of the potential anomaly.

22. The computer-readable storage medium of claim 16, wherein the initial scan plan is dynamically modified based on detection of another potential anomaly in a second biological lifeform.

23. The method of claim 17, wherein the one or more operations comprise analyzing the second MR signals to improve an accuracy of the detected potential anomaly based on one or more of: the medical history; the MR-scan history; and a second template of the potential anomaly.

* * * * *